United States Patent [19]

Kit et al.

[11] Patent Number: 5,292,653
[45] Date of Patent: Mar. 8, 1994

[54] EQUINE HERPESVIRUS 1 TK MUTANTS

[75] Inventors: Malon Kit; Saul Kit, both of Houston, Tex.

[73] Assignees: NovaGene, Inc.; Baylor College of Medicine, both of Houston, Tex.

[21] Appl. No.: 413,040

[22] Filed: Sep. 27, 1989

[51] Int. Cl.[5] .................. C12N 7/00; C12N 15/00
[52] U.S. Cl. .................. 435/235.1; 435/172.3; 435/320.1; 935/32
[58] Field of Search ............ 435/320.1, 69.1; 935/32, 22

[56] References Cited
PUBLICATIONS

Lowe et al. (1987) Proced. Natl. Acad. Sci. 84, 3896–3900.
Robertson et al (1988) Nucleic Acids Res 16, 11303–11317.

Primary Examiner—Elizabeth C. Weimar
Assistant Examiner—Deborah Crouch
Attorney, Agent, or Firm—Sughrue, Mion, Zinn, Macpeak & Seas

[57] ABSTRACT

The present invention relates to Equine Herpesvirus Type 1 mutants which fail to produce any functional thymidine kinase as a result of a deletion and/or insertion in the EHV-1 thymidine kinase gene.

27 Claims, 7 Drawing Sheets

Fig. 3

| | | | | | | |
|---|---|---|---|---|---|---|
| CGGGGGTAGC | GTTCTCGCCA | GCAACCTGCA | CGAGTCATGT | AGCTGTCGCA | TGCCCCCCTT | 60 |
| CCGCTGTAGA | TTTTTACTCG | CGGTGTTCAT | ATTTTTGGAA | AAGCGACACG | TTTTTAGCTC | 120 |
| TATTAGGATG | CACACTCCCT | TGGCGTCAGA | ACCCTTTCCA | AATTGCACGG | TACAGACACA | 180 |
| ATCCGGGCGC | CGCTGTCCGA | GGTTAACCTC | AAAGGCCAGA | GACACGCCCA | GTGCCGTTTT | 240 |
| AAGAGTTTCC | GCTGGCACCA | GTTCACTAAA | AAGGGGAGCA | AGCCTCTCTC | CGTACACGCC | 300 |
| GTTTCGCTTG | CGCTTGCCA | GGTCTTGAAC | CATCGCGTTA | TAGAAGCGGT | TGTGGCACCG | 360 |
| TATACCAGCT | CTGAGTCTGC | TTCTAGCTGT | CAGACGCTGT | CTACGTTTCA | TTTTCAGAAA | 420 |
| TCAATGGCGG | CTCGCGTACC | TTCCGGGGAA | GCTCGACGGA | GCGCCAGCGG | GGCGCCGGTC | 480 |
| AGGCGGCAAG | TAACAATAGT | TAGAATTTAC | CTCGATGGGG | TCTACGGCAT | CGGCAAGAGC | 540 |
| ACGACTGGAC | GAGTTATGGC | ATCGGCTGCG | AGTGGAGGAA | GTCCAACTCT | ATACTTTCCT | 600 |
| GAGCCTATGG | CGTACTGGCG | GACTCTCTTT | GAAGCGGACG | TAATTAGTGG | TATTTACGAC | 660 |
| ACCCAGAACC | GGAAACAGCA | GGGAGATTTG | GCGGCTGATG | ACGCGGCGTC | AATAACGGCG | 720 |
| CACTACCAGA | GCCGCTTTAC | CACGCCCTAC | CTTATCCTAC | ACGATCACAC | ATTTGGGTTG | 780 |
| TTTGGGGGTG | ACAGCCTACA | GCGTGGGACA | AGACCAGACC | TAACCGTCGT | TTTTGACCGC | 840 |
| CACCCAGTCG | CCTCTGCCGT | GTGCTTTCCC | GCCGCTCGCT | ACCTCATCGG | AGACATGTCC | 900 |
| ATGTGCGCGC | TGATTGCCAT | GGTTGCCACC | CTACCCAGGG | AACCGCAAGG | CGGAAACATC | 960 |
| GTGGTTACCA | CCCTCAATGT | GGACGAGCAC | GTGCGAAGAC | TGCGCACCCG | CGCCAGAATC | 1020 |
| GGGGAACAGA | TTGACATGAA | GCTAATCGCC | ACACTGCGAA | ACGTGTACTC | TATGCTCGCT | 1080 |
| AATACTAGCA | ACTTTTTGCG | CTCCGGGAGA | GTATGGCGCG | ACGGCTGGGG | GGAGTTGCCC | 1140 |
| CTTTCGTGCG | AGACCTATAA | ACATCGCGCA | ACGCAGATGG | ACGCCTTCCA | GGAGCGCGAA | 1200 |
| TCTCCTGAGC | TGAGCGACAC | GTTGTTTGCC | ATGTTTAAGA | CTCCCGAGCT | GCTAGACGAT | 1260 |
| CGTGGAGTGA | TATTGGAAGT | TCACGCCTGG | GCGCTTGACG | CGCTGATGCT | AAAGCTGCGC | 1320 |
| AACCTGAGTG | TTTTTTGCGC | TGATCTGAGC | GGGACTCCGC | GCCAGTGTGC | TGCAACCGTG | 1380 |
| GAGTCTCTAA | TACCCCTCAT | GAGCAGCACC | CTCTCCGATT | CGGAGTCGGC | CTCCTCCCTG | 1440 |
| GAGCGGGCCG | CGCGCACCTT | CAACGCCGAG | ATGGGCGTCT | GAAACTATAT | GTAATGTTTG | 1500 |
| TTGTGCCAGT | GTAATAATTA | TGAAATAAAG | ATTCCTTTGC | CTATATCCCT | ATACCGCCTG | 1560 |
| TGTGTCCAGT | GTGTAAACTT | CCAGGTTCTA | GTTTTGGGGA | TATATAAGTG | GCTGTGACCT | 1620 |

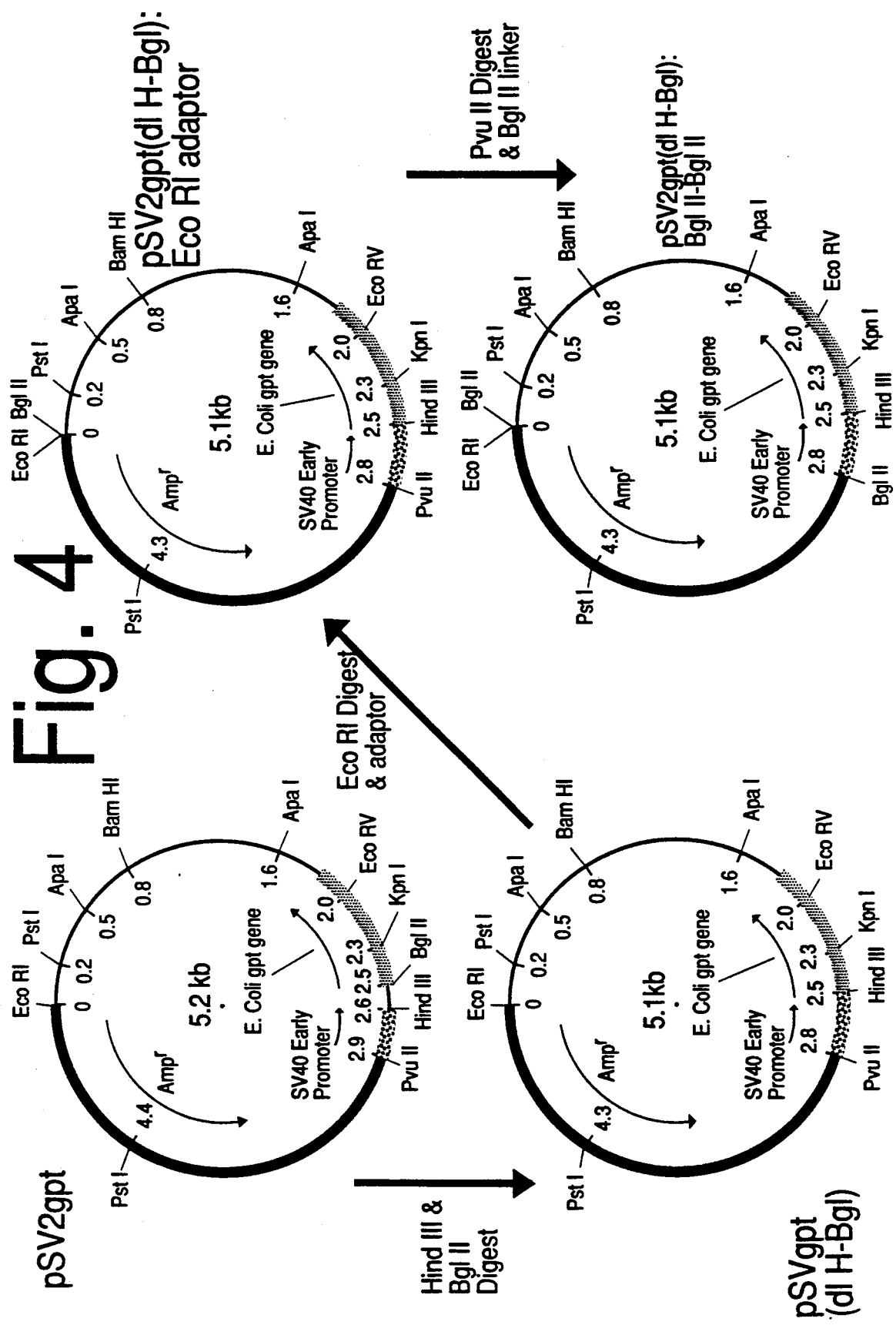

EQUINE HERPESVIRUS 1 TK MUTANTS

FIELD OF THE INVENTION

The present invention relates to Equine Herpesvirus Type 1 (hereinafter "EHV-1") mutants which fail to produce any functional or antigenic non-essential EHV-1 gene product, such as the EHV-1 thymidine kinase, as a result of a deletion and/or insertion in a non-essential EHV-1 gene; Equine Herpesvirus Type 1-based viral vectors; and vaccines containing the same.

BACKGROUND OF THE INVENTION

I. Equine Herpesviruses

There are four known equine herpesvirus types (O'-Callaghan, D. J. et al, *In: The Herpesviruses*, Ed. Roizman B., Plenum Press, New York, 2:215-318 (1983); Studdert, M. J. et al, *Science*, 214:562-564 (1981); and Studdert, M. J. et al, *Arch. Virol.*, 91:375-381 (1986)). Equine Abortion Virus, also known as Equine Herpesvirus Type 1 (hereinafter "EHV-1", is a major cause of respiratory disease and abortion in horses. Equine Herpesvirus Type 2 is a ubiquitous, slowly growing cytomegalovirus which is not identified with any known disease syndromes in horses. Equine Herpesvirus Type 3 is the agent of genital exanthema of mares and stallions. Equine Herpesvirus Type 4 causes recurrent respiratory disease which can impair racing performance. Each of these equine herpesvirus types are fundamentally distinct in terms of associated clinical symptoms, histopathology serology, nucleic acid homology, and epidemiological patterns.

II. Equine Herpesvirus Type 1

EHV-1 causes abortion in pregnant mares, most frequently during the last few months of the pregnancy term. Abortion usually occurs in the absence of overt clinical disease in the mares, and is attributable to reactivation of latent EHV-1 infection. Abortion "storms" occur in herds where the virus has not circulated in several years, and a large population of susceptible animals are present. The potential severity of disease from EHV-1 is exemplified by the 1986 abortion storms from EHV-1 which decimated the famed Austrian Lippinzaner breeding herd (Chowdhury, S. I., et al, *Arch. Virol.*, 90:273-288 (1986)). Aborted fetuses show evidence of bronchopneumonia as the primary histopathology. EHV-1 also causes an often fatal bronchopneumonia during perinatal infection of foals. Further in immunologically naive weaned foals and yearlings, infection by EHV-1 causes a respiratory syndrome characterized by fever, rhinorrhea, pharyngitis, and tracheobronchitis. In addition, bacterial superinfection may cause lymphoid abscesses or bronchopneumonia. Immunity from reinfection with EHV-1 is short lived, and recurrent disease from reactivation of latent infection is also believed to occur.

III. Known EHV-1 Vaccines

Many live and inactivated EHV-1 vaccines have been described, though few have been commercialized (Campbell, T. M., et al, *Vet. Bull.*, 53:135-145 (1983); U.S. Pat. No. 4,225,582; U.S. Pat. No. 4,083,958; and U.S. Pat. No. 3,725,542).

There are two equine vaccines most commonly used throughout the world for the control of EHV-1 infection. However, each of these EHV-1 vaccine possess disadvantageous characteristics. More specifically, a modified-live EHV-1 vaccine has been shown to produce seroconversion after vaccination (Bass, E. P., *Proc. 24th Ann. Conf. Am. Assoc. Equine Pract.*, 65-74 (1978)). However, this EHV-1 vaccine has been incriminated in the possible induction of post-vaccination abortion when used in pregnant mares (Burrows, R. et al, *Proc. 24th Ann. Conf. Am. Assoc. Equine Pract.*, 17-29 (1978)). An inactivated EHV-1 vaccine is available which also produces seroconversion and provides partial protection against abortion. However, this vaccine can not induce as broad an immunological response as the modified-live virus vaccine. Moreover, inactivated EHV-1 vaccines are associated with undesirable local reactions, such as inflammation and sterile abcesses in up to 10% of the vaccinated animals (Collin, A., *Vet. Rec.*, 124:496 (1989)). Further, both of the above EHV-1 vaccines are disadvantageously characterized by a short duration of immunity, requiring revaccination every three months (Bryans, J. T., *Am. J. Vet. Res.*, 41(11):1743-1746 (1980)). In addition, none of the existing EHV-1 vaccines are known to have a deletion in the gene of a major non-essential antigen which might be used as a marker to serologically distinguish vaccinated animals from infected animals.

IV. Attenuated Properties of Thymidine Kinase-Negative Herpesvirus Mutants

Herpesvirus-encoded thymidine kinase (hereinafter "TK") enzymes are distinct from host cell TK enzymes in immunological and biochemical properties. Herpesvirus TK enzymes facilitate herpesvirus replication in non-dividing cells. Because many herpesviruses are neurotropic viruses normally capable of both productive and latent infection in non-dividing neural cells, it has been hypothesized that thymidine kinase-negative (hereinafter "$tk^-$") virus mutants may be less neurovirulent than wild-type thymidine kinase-positive (hereinafter "$tk^+$") strains.

Attenuation of viral virulence in $tk^-$ mutants has been found in herpes simplex virus type 1 and type 2, in herpesvirus tamarinus, in pseudorabies virus (hereinafter "PRV"), and in infections bovine rhinotracheitis virus (hereinafter "IBRV") (Klein, R. J., *Arch. Virol.*, 72:143-160 (1982); Kit, S. et al, *J. Med. Virol.*, 12:25-36 (1983); Kit, S. et al, *Am. J. Vet. Res.*, 46:1359-1367 (1985); Stanberry, L. R. et al, *J. Virol.*, 55:322-328 (1985); U.S. Pat. No. 4,514,497; and U.S. Pat. No. 4,703,011).

V. Thymidine Kinase-Negative Mutagen-Induced and Spontaneous Herpesvirus Mutants Several different types of herpesvirus mutants deficient in TK-inducing activity are known. Many of these mutants induce the synthesis of normal sized TK polypeptides, but without any functional TK activity. These mutants either have changed amino acids at the active centers of the enzyme or mutations that alter polypeptide folding. Other mutants, e.g., HSV-1 (B2006), fail to induce the production of any TK polypeptide, possible as a result of nonsense mutations at codons near the amino terminus of the polypeptide. Still other mutants induce inactive truncated (or shortened) polypeptides because of translation-terminating (nonsense) codons in the middle of the tk gene. This type of mutation can be "suppressed" with "suppressor tRNA's" so that partial TK activity is restored. Yet other types of mutants induce TK enzymes with altered nucleotide substrate specificities. For example wild-type (i.e., non-mutant) HSV-1 viruses induce TK enzymes that efficiently catalyze the phosphorylation of thymidine, deoxycytidine and the nucleoside analogs, bromovinyldeoxyuridine and acyclovir. However while HSV-1 mutants with altered substrate specificities induce TK activities with reduced, but significant thymidine phosphorylating activity, these mutants may be deficient in the capacity to phosphorylate acyclovir or bromovinyldeoxyuridine to their triphosphates (Fyfe, J. A., et al. *Molec. Pharmacol.*, 24:316-323 (1983); and Kit, S. et al, *Antimicro. Agents* and *Chemother.*, 31:1483-1490 (1987)). These mutants have changed amino acids at the nucleoside binding sites of the enzymes. Hence, affinities for nucleoside or mononucleotide substrates are reduced in comparison with that of wild-type HSV-1 encoded TKs.

Mutagen-induced and spontaneous tk⁻herpesviruses have been described for HSV-1 and HSV-2 PRV, IBRV and EHV-1 (U.S. Pat. No. 4,514,497; U.S. Pat. No. 4,703,011; Kit, S. et al, *Antiviral Res.*, 7:53-67 (1987); and Allen, G. P. et al; *Virol.*, 90:351-359 (1978)).

VI. Thymidine Kinase-Negative Deletion and/or Insertion Herpesvirus Mutants tk⁻herpesviruses with genetically engineered deletions and/or insertions within the coding region functional TK polypeptide. tk⁻herpesviruses with genetically engineered deletions and/or insertions in the tk gene are superior to mutagen-induced tk⁻mutants (U.S. Pat. No. 4,514,497: and U.S. Pat. No. 4,569,840) or spontaneous mutants for the following reasons.

First, the herpesvirus deletion and/or insertion mutants have absolutely no TK-inducing activity because (i) the deletion and/or insertion of amino acid coding sequences changes the tertiary structure and/or substrate binding sites of the TK enzyme in such a way that the catalytic function is irrevocably lost; and (ii) those nucleotide deletions and/or insertions that are not divisible by 3 change the translational reading frame of the virus gene encoding the TK polypeptide. In contrast, mutations, such as found in mutagen-induced and spontaneous mutants, usually involve single nucleotide changes. As a result these mutations frequently exhibit partial TK-inducing activity. This is inappropriate for a vaccine because mutants with partial TK-inducing activity are often virulent or have a greater capacity to establish latent ganglionic infections (Gordon, Y. et al, *Arch. Virol.*, 76:39-49 (1983); Klein, R. J., *Arch. Virol.*, 72:143-168 (1982); Tenser, R. B., et al, *Virol.*, 112:328-334 (1981); and Coen, P. M. et al, *Virol.* 168:221-231 (1989)).

Second, tk⁻herpesviruses with genetically engineered deletions and/or insertions in the tk gene cannot revert to tk⁺. In contrast, tk⁻mutagen-induced and spontaneous mutants which contain only single nucleotide changes in the tk gene can revert to tk⁺. The tk⁺revertants have restored virulence (Kit, S. et al, *Am. J. Vet. Res.*, 46:1359-1367 (1985)). Further, working pools of tk⁻mutagen-induced and spontaneous mutants can contain spontaneous tk⁺revertants at a frequency of $10^{-3}$ to $10^{-5}$. These tk⁺revertants can then have a selective advantage for in vivo replication over the tk⁻mutants. Most mutagen-induced tk⁻herpesvirus mutants have the potential to revert, even though the reversion frequency may be lower than the reversion frequency for spontaneous mutants, i.e.. on the order of about $10^{-5}$ to $10^{-7}$ p.f.u./ml (Campione-Piccardo, J. et al, *J. Virol.*, 31:286-287 (1979)). Since a typical vaccine dose comprises up to $10^7$ p.f.u./ml the formulation will inevitably be contaminated with trace quantities of infectious virulent virus. This can result in the undesired effect of introducing virulent virus into disease free herds or regions, where vaccination is practiced prophylactically.

Third, tk⁻herpesviruses with genetically engineered deletions and/or insertions in the tk gene can be distinguished from virulent field strains and from other vaccine strains by their tk⁻phenotype, by their restriction endonuclease patterns, and by Southern blotting molecular hybridization patterns (Kit., S. et al, *Am. J. Vet. Res.*, 46:1359-1367 (1985)). These distinctions have practical importance. For example, if a vaccinated animal developes disease, it is important to know whether the vaccine virus caused the disease or whether infection by a virulent field strain caused the disease.

VII. Identification of Non-essential Genes

Heretofore, it has only been known that the EHV-1 genome, (i) is a double stranded, linear DNA genome of about 100 mega-daltons (159 kilobase pairs (hereinafter "kb" or "Kbp"); (ii) has an overall molar guanine plus cytosine content of about 56%; (iii) is composed of L and S components which can exist in two isomeric forms; and (iv) is cleaved by BglII, EcoRI, and BamHI restriction endonucleases to 16, 16, and 21 fragments, respectively. The size of these fragments and their arrangement on the physical map of EHV-1 have also been described (see FIG. 1) (Whalley, J. M. et al, *J. Gen. Virol.*, 57:307-323 (1981)). Further, a fine map and sequence of the EHV-1 origin of replication and the EHV-1 gp13 and gp 14 glycoproteins has been described (Baumann, P. et al, *J. Virol.*, 63(3):1275-1283 (1989); Allen, G. et al, *J. Virol.*, 62(8):2850-2858 (1988); and Whalley, J. M. et al, *J. Gen. Virol.*, 70:383-394 (1989)); as well as a general map of other EHV-1 glycoproteins, e.g., gp2, gp10, and gp21/22a (Allen, G. P. et al, *J. Virol.*, 61(8):2454-2461 (1987)).

One method employed to map EHV-1 glycoprotein genes involves the cloning of random DNA fragments of EHV-1 in the lambda gt11 expression vector as fusion proteins with β-galactosidase. The resulting recombinant phage are screened for reactivity to monoclonal antibodies specific for each glycoprotein. This technique is not applicable for identifying the EHV-1 tk gene because of the unavailability of monoclonal antibodies to EHV-1 TK and because of the difficulty in preparing monoclonal antibodies to TK.

An alternative method for mapping EHV-1 glycoprotein genes involves using the corresponding glycoprotein of another herpesvirus e.g., HSV-1, as a probe to detect sequence homology by DNA-DNA hybridization. This technique is only applicable for identification of EHV-1 glycoprotein genes which are highly conserved.

To identify fragments encoding herpesvirus tk genes, one or more of the following methods have previously been used: (1) molecular hybridization experiments in which labeled DNA fragments from a known viral tk gene and DNA fragments from the unknown virus are hybridized to detect homologous nucleotide sequences; (2) biochemical transformation of mutant tk⁻cells (e.g.. mouse fibroblast LM(TK⁻)) with tk⁺plasmids containing the putative tk gene so as to produce the tk⁺phenotype in the cells; (3) transfection or microinjection of hybrid plasmids containing the putative tk gene into LM(TK⁻) cells or mouse or frog eggs and then assaying for transient expression of TK enzyme activity: and (4) marker transfer experiments with infectious DNA from a tk−mutant virus and hybrid plasmids containing the tk+gene (Scangos, G. et al, *Gene*, 13:1–10 (1981); Brinster, R. L. et al, *Nature*, 296:39–42 (1982); Otsuka, H. et al, *Virol.*, 113:196–213 (1981); Kit, S. et al, *Virol.*, 113:452–464 (1981); Weir, J. P. et al, *Proc. Natl. Acad. Sci.*, USA, 79:1210–1214 (1982); Dubbs, D. R. et al, *Virol.*, 126:408–411 (1983); Otsuka, H. et al, *Antiviral Res.*, 2:301–311 (1982); McKnight, S. L., *Nucl. Acids Res.*, 8:5931–5948 (1980); Capecchi, M. R., *Cell*, 22:479–488 (1980)).

However, it is unpredictable which, if any, of the above general methods could be employed to the identify the DNA fragment which encodes the EHV-1 tk gene. More specifically, high specific activity, $^{32}$P-labeled probes made by nick translating clones of HSV, PRV, IBRV and herpesvirus tamarinus tk genes do not hybridize to EHV-1 DNA fragments. Thus, the technique of molecular hybridization is not applicable to the EHV-1 tk gene. That is, there is substantially no homology between the tk genes of various herpesvirus species, i.e., the nucleotide sequences of the tk genes and the amino acid sequences of the TK enzymes of the various herpesvirus species are dissimilar. Further, biochemical transformation experiments in which cloned IBRV DNA fragments are transfected into tk−mutant mouse (LM(TK−)) or rabbit (RAB(BU)) cells do not yield colonies of tk+cells containing integrated IBRV DNA sequences (U.S. Pat. No. 4,703,011). Likewise, transfection of hybrid plasmids containing IBRV DNA fragments into RAB(BU) cells does not lead to the transient expression of TK activity (U.S. Pat. No. 4,703,011). In addition as discussed in detail below the conventional marker rescue methods are insufficient to enable one to identify the EHV-1 restriction fragment encoding the EHV-1 tk gene.

On the other hand, it was surprisingly found in the present invention that a transient expression assay for the EHV-1 tk gene in transfected tk−host cells could be used to successfully define the approximate boundaries of the EHV-1 tk gene and obtain the sequence of the EHV-1 tk gene.

VIII. The Unpredictability Associated with the Construction of Recombinant Viruses General approaches for the genetic engineering of herpesviruses with deletions (insertions) in the coding region of the tk gene (non-essential gene) are known. These methods have been used to obtain tk−deletion mutants of HSV-1, HSV-2, herpesvirus tamarinus. PRV and IBRV (Smiley, J. R., *Nature*, 385:333–335 (1980); Post, L. E. et al, *Cell*, 24:555–565 (1981); Post, L. E. et al, *Cell*, 25:227–232 (1981); McDermott, M. R. et al, *J. Virol.*, 51:747–753 (1983); Kit, S. et al, *J. Med. Virol.*, 12:25-36 (1983); Kit, S. et al, *Am. J. Vet. Res.*, 46:13259–1367 (1985): U.S. Pat. No. 4,769,331; U.S. Pat. No. 4,514,497; and U.S. Pat. No. 4,703,011).

However, the general approaches described in the above-cited references are not directly useful in the preparation of EHV-1 non-essential−(particularly tk−) deletion and/or insertion mutants, much less EHV-1-based viral vectors, since there is no teaching or suggestion therein of: (1) the boundaries of the EHV-1 tk gene and its nucleotide sequence, (2) adequate methods for introducing detectable genetic exchanges between the EHV-1 genome and exogenous DNA, and (3) adequate methods for isolating the desired recombinants from the recombination pool of viruses which contains an overwhelming proportion of the parental EHV-1 or tk+EHV-1 and spontaneous tk−mutants.

The existence of the cellular uptake of exogenous DNA and the in vivo recombination of an organism's genome with the exogenous DNA was discovered in 1944 by Avery, O. T. et al, *J. Exp. Med.*, 79:137 (1944), who demonstrated that the capsule characteristics of pneumococcal bacteria could be genetically altered (transformed) by the uptake of exogenous DNA from a different pneumococcal strain. However, only a few organisms are competent, i.e., capable of taking up foreign DNA, without special treatments. The number of species which can be made competent and transformed have been slowly and incrementally extended by the development of new methods.

The uptake of exogenous nucleic acid by mammalian cells was first demonstrated with RNA viruses (Colter, J. S. et al, *Nature*, 179:859–860 (1957)). The uptake of exogenous nucleic acid and the genetic transformation of mammalian cells was demonstrated by Syzbalski, W. et al, *Univ. Mich. Med. Bull.*, 28:277 (1962). Improved methods of achieving uptake of exogenous DNA were achieved using DEAE-mediation (Warden, D. et al, *J. Gen. Virol.*, 3:371–377 (1968)), and calcium phosphate-mediatation (Graham, F. L. et al, *J. Virol.*, 52:456–467 (1973)). More recent techniques have involved microinjection (Anderson, W. F. et al, *Proc. Natl. Acad. Sci.*, USA, 77:5399–5403 (1980)); protoplast fusion (Rassoulzadegan, M. et al, *Nature*, 295:257–259 (1982)); electroporation (Potter, H. et al, *Proc. Natl. Acad. Sci.*, USA, 81:7161–7165 (1984)); microprojectiles (Klein, T. M. et al, *Nature*, 327:70–73 (1987)); laser micropuncture (Tao, W. et al, *Proc. Natl. Acad. Sci.*, USA, 84:4180–4184 (1987)): scrape loading (Ortiz, D. et al, *Mol. Cell. Biol.*, 7(8):3012–3017 (1987)); receptor-mediated endocytosis (Wu, G. Y. et al, *Biochem.*, 27:887–892 (1988)); detergents (Aubin, R. J. et al, *Somat. Cell and Mol. Gen.*, 14(2):155–167 (1988)); and liposomes (Schaefer-Ridder, M. et al, 215:166–168 (1982)).

The fundamental experience over the past 45 years in this art is that every new system of study, being intrinsically distinctive in nature, imposes unpredictable problems and extensive experimentation is required in order to exploit genetic exchanges. This diversity of needs and solutions is manifested by the ongoing proliferation of gene transfer methods.

The existence, detectability and applicability of gene transfer methods are determined by: (a) the extent to which exogenous DNA is taken up by a cell, (b) the frequency of recombination, and (c) the nature and availability of suitable selection and enrichment procedures, i.e., the nature and availability of suitable methods of identifying and isolating the small number of genetically altered organisms from the overwhelming background of native organisms present. Key factors of a unique nature that effect the above parameters are: (1) the type of recombination either homologous or non-homologous (the type of recombination is effected by the method by which the exogenous DNA is introduced into cells), (2) the nature of the specific exogenous DNA, and (3) the nature of the specific recipient cell.

In vivo genetic exchanges are infrequent events. Homologous recombination after uptake of foreign DNA can be relatively inefficient with available methods (Stow, N. D. et al, *J. Virol.*, 28(1):182–192 (1978)) or so infrequent as to be undetectable with available methods (Smithies, O. et al, *Nature*, 317:230-234 (1985)).

The first demonstration of in vivo homologous recombination between a herpesvirus genome and DNA fragments was with HSV-1 (Wilkie, N. M. et al, *Cold Spring Harbor Symposium on Quantitative Biology*, Vol. XXXIX, pp. 657-666 (1975)). This marker rescue procedure involved the transfection of cells with a calcium phosphate-DNA precipitate of a DNA fragment containing a mutant gene, followed by superinfection of the cells with a wild-type virus. Since only 0.1 to 1.0% of the transfected cells were competent to take up the calcium phosphate-DNA precipitate the resulting population of virus consisted of 100 to 1000 fold more wild-type virus than the mating pool of virus from cells which took up the calcium phosphate-DNA precipitate. It is within the mating pool that homologous recombination occurs. Thus, this method only allows the detection of recombination for genes that do not spontaneously mutate or significantly revert. This is because the background of spontaneous mutants revertants and wild-type virus is so large that the proportion of the virus population containing recombinant virus is below the limits of detectability (Wilkie, N. M. et al, *Cold Spring Harbor Symposium on Quantitative Biology*, Vol. XXXIX, pp. 657-666 (1975)).

As a result, a modified marker rescue method for HSV-1 was developed so as to identify DNA fragments containing genes that spontaneously mutate or revert at high frequency, such as the tk gene (Stow, N. D. et al, *J. Virol.*, 28(1):182-192 (1978)). In this method, co-transfection of infectious HSV-1 DNA and DNA fragments was carried out. By this method the resulting population of virus arose only from cells which took up the exogenous DNA. thereby improving the detectability of recombination by 100 to 1000 fold.

The subsequent genetic engineering of recombinant herpesviruses with deletions and/or insertions in the viral genome described in the art have all relied upon the marker rescue method discussed above. In this marker rescue method transfection and marker rescue was carried out in permissive cells. As used herein, "permissive cells" are those cells which support EHV-1 virus growth to high titers, i.e., about greater than $10^6$ to $10^8$ p.f.u./ml. The permissiveness of the cells depends on the virus strain employed and can be readily ascertained by one skilled in the art. It has been surprisingly found by Applicants that this marker rescue method is inadequate for obtaining recombinant EHV-1. That is, it has been surprisingly found by Applicants that the detectability of recombination for EHV-1 by the above marker rescue method is influenced by (i) the level of infectivity of the viral DNA, i.e., the number of cells in which the viral DNA initiates a complete productive viral life cycle leading to the production of infectious viral particles, and (ii) the cell type in which recombination is to occur.

It has been found in the present invention that the rate of recombination of EHV-1 DNA and DNA fragments can be increased and that EHV-1 recombinant viruses can be obtained through a modified marker rescue procedure which involves transfection of DNA into cells (a) in which EHV-1 DNA infectivity is high. (b) which are semi-permissive and (c) which are immortalized cell lines. As used herein "semi-permissive cells" are those cells which support EHV-1 virus growth to levels intermediate between permissive and non-permissive cells i.e., from about $10^4$ up to $10^6$ p.f.u./ml. The semi-permissiveness of cells is dependent on the virus strain employed and can be readily ascertained by one skilled in the art.

Prior to the present invention, it was not expected that the recombination rate would be effected by the level of infectivity of EHV-1 DNA. That is, it is known that with vaccinia virus, the efficiency of marker rescue and the rate at which recombinant viruses are generated are not increased by glycerol or DMSO boosts. Glycerol and DMSO boosts have been found to increase transfection efficiencies (Mackett, M. et al, *J. Gen. Virol.*, 67:2067-2083 (1986)).

Recombination has generally been found by Applicants to be undetectable unless the viral DNA has an infectivity of greater than 100 p.f.u./µg of DNA. The level of infectivity of the viral DNA is effected by undefined experiment to experiment variations, by the host cell line employed to take up the exogenous DNA, and by the strain of virus employed. For example, the infectivities of HSV-1, HSV-2 and PRV DNA in BHK cells is from 5000 to 6000 p.f.u./µg of DNA (Wilkie, N. M. et al, *Cold Spring Harbor Symposium on Quantitative Biology*, Vol. XXXIX, pp. 657-666 (1975)). The PRV and IBRV DNA, prepared in U.S. Pat. No. 4,514,497 and U.S. Pat. No. 4,703,011 by the method of Pignatti, P. F. et al, *Virol.*, 93:260-264 (1979), has been found by Applicants to have an infectivity in RAB-9 cells of about 1000 p.f.u./µg of DNA. RAB-9 cells are permissive for PRV and IBRV (U.S. Pat. No. 4,514,497; and U.S. Pat. No. 4,703,011).

However, it has been found by Applicants that EHV-1 DNA prepared by the method of Pignatti, P. F. et al, *Virol.*, 93:260-264 (1979), as in U.S. Pat. No. 4,514,497 and U.S. Pat. No. 4,703,011, has an infectivity which is consistently 10 to 100 fold lower than HSV-1. HSV-2, marmosett herpesvirus, PRV or IBRV DNA in permissive cells. The lower level of infectivity of EHV-1 DNA has, prior to the present invention, impeded the successful isolation of EHV-1 recombinants.

Although a method for purifying EHV-1 DNA with a higher level of infectivity in certain permissive cell types is known (Whalley, J. M. et al, *J. Gen. Virol.*, 57:307-313 (1981)), prior to the present invention, there was no teaching or suggestion of the need to optimize the level of infectivity to obtain recombination between EHV-1 DNA and transfected DNA fragments.

It was found, for the first time, in the present invention, that the level of infectivity of EHV-1 DNA is sufficiently increased in semi-permissive EHV-1 host cell lines so as to achieve detectable recombination.

Applicants have also surprisingly found that the known marker rescue procedures did not yield observable recombinant EHV-1 when EHV-1 DNA and DNA fragments were transfected into equine cells. Equine cells are permissive for EHV-1 and were believed to be the preferred cell type for recombination because most EHV-1 strains demonstrate greater growth therein.

It should be noted that the available equine cells used in tissue culture are not immortalized cells. Rather, they are primary and secondary cultures which undergo senescence after a finite number of cell generations. Recombination rates of homologous DNA fragments in secondary cell cultures can be less that 10% of the level present in similar immortalized cell lines (Finn, G. K. et al, *Mol. Cell. Biol.*, 9:4009-4017 (1989)).

It was found, for the first time in the present invention that recombination of transfected EHV-1 DNA and DNA fragments could be detected and recombinant EHV-1 obtained by using an immortalized cell line, e.g., RAB-9. Although RAB-9 cells were used to successfully obtain PRV and IBRV recombinants (U.S. Pat. No. 4,514,497; and U.S. Pat. No. 4,703,011). it was surprising that RAB-9 cells could be employed to obtain EHV-1 recombinants. This is because while RAB-9 cells are permissive for PRV and IBRV, they are semi-permissive for EHV-1. Semi-permissive cells only produce about $10^{-4}$ to $10^{-2}$ as many virus particles as permissive cells. RAB-9 cells have been found to be preferred in the present invention because EHV-1 infectivity is increased therein and because recombination rates are believed to be increased by virtue of immortalization and semi-permissiveness.

It was also found, for the first time, in the present invention that the resulting recombinant EHV-1 population yield will only be large enough for selection and screening if the semi-permissive EHV-1 host cells are overlaid with permissive EHV-1 host cells immediately after co-transfection of the infectious EHV-1 DNA and the DNA fragments. The use of the overlayer of permissive EHV-1 host cells has been found in the present invention to be necessary. That is, even though the recombination rate is sufficient in semi-permissive EHV-1 host cells, the yield of infectious particles is too low to be able to screen for and isolate the recombinant viruses. The use of an overlayer of permissive EHV-1 host cells allows for the production of a high yield of EHV-1 particles, thus enabling the screening for and isolation of the recombinant viruses.

IX. Marker Vaccines

It has been recognized that improved animal disease control can be achieved with marker vaccines which allow serological differentiation between vaccinated animals and animals infected with virulent virus (U.S. Pat. No. 4,753,884, describing a PRV marker vaccine: and U.S. patent application Ser. No. 07/116,197, filed Nov. 3, 1987, describing a IBRV marker vaccine). These marker vaccines were genetically engineered so that they fail to produce a viral antigen which is non-essential for viral growth.

Prior to the present invention, the genetic engineering of EHV-1 marker vaccines had not been possible because, as discussed above the heretofore known marker rescue method is inadequate for obtaining EHV-1 recombinant viruses. Thus, for the first time, using the knowledge of the present invention and the knowledge of EHV-1 genes which are homologous to the marker antigens employed for PRV and IBRV, e.g., EHV-1 gp13 (Allen, G. P., et al, *J. Virol.*, 62:2850–2858 (1988)), an EHV-1 marker vaccine can be genetically engineered.

X. Viral Vectors

During the last few years, recombinant DNA technology has permitted the construction of chimeric viruses which express genetic information from more than one virus.

A variety of unique viral-based vectors have been developed such as adenovirus-based viral vectors (Ruether, J. E. et al, *Mol. Cell. Biol.*, 6:123–133 (1986); and Haj-Ahmad, Y. et al, *J. Virol.*, 57:267–274 (1986)); herpes simplex virus-based viral vectors (Smith, M. et al, *Proc. Natl. Acad. Sci., USA*, 81:5867–5870 (1984); and Smiley, J. R. et al, *J. Virol.*, 61:2368–2377 (1987); European Patent Publication No. 0168662; and European Patent Publication No. 0176170); Herpes saimiri virus-based viral vectors (Desrosiers, R. C. et al, *Mol. Cell. Biol.*, 5:2796–2803 (1985)); baculovirus-based viral vectors (van Wyke Coelingh, K. L. et al, Virol., 160:465–472 (1987); Miyamoto, C. et al, *Mol. Cell. Biol.*, 5:2860–2865 (1985); Smith, G. E. et al, *Proc. Natl. Acad. Sci.*, USA, 82:8404–8408 (1985); Smith, G. E. et al, *Mol. Cell. Biol.*, 3:2156–2165 (1983); Matsuura, Y, et al, *J. Gen. Virol.*, 68:1233–1250 (1987); and Kang, C. Y. et al, *J. Gen. Virol.*, 8:2607–2613 (1987)); nuclear polyhedrosis virus-based viral vectors (Hu, S. L. et al, J. Virol., 61:3617–3620 (1987); and Marumoto, Y. et al, *J. Gen. Virol.*, 68:2599–2606 (1987)); BK-based viral vectors (Caputo, A. et al, *J. Gen. Virol.*, 69:459–566 (1988)); and poliovirus-based viral vectors (Evans, D. J. et al, *Nature*, 339:385–388 (1989)).

The use of viral-based vectors as vaccines is advantageous over subunit vaccines because replication of the viral-based vectors within the host amplifies the amount of foreign antigen being expressed thereby, often increasing both cell-mediated and humoral immunogenic responses to the foreign antigen. In addition, the expression of foreign antigens within infected cells of the immunized host provides for post-translational modifications of the foreign antigen. Thus, antigen presentation more closely resembles that occurring during natural infection with the pathogen from which the foreign antigen is derived. Further, the use of a safe, live-attenuated virus as a vector allows for the immunization against the pathogen from which the foreign antigen is derived.

Viral-based virus vectors offer several significant advantages. First, immunization against more than one disease is possible with a single virus strain. This creates economy of production. Second, for many vaccines, two or more different modified-live viruses cannot be employed in combination in a single formulation because the replication of the viruses in the host causes mutual interference, and thereby impairs immunization. This situation is circumvented with viral-based vectors because there is only a single replicating genome. Third, vaccines against causative agents of infectious disease, such as viruses and bacteria, for which vaccines have not previously been available or feasible, may for the first time be developed using viral-based vectors which express the antigens of the causative agents of infectious disease. This is because the only component of the causative agents of the infectious disease which is carried by the viral-based vector is the gene coding for the antigen of the causative agent of disease which is responsible for eliciting immunity. Other components of the causative agents of infectious disease that are responsible for the pathobiology of the disease are eliminated from the viral-based vector.

The most extensively developed and exploited viral-based vectors are the vaccinia virus-based viral vectors (Mackett, M. et al, *Proc. Natl. Acad. Sci.*, USA, 79:7415–7419 (1982); Panicali, D. et al, *Proc. Natl. Acad. Sci.*, USA, 79:4927–4931 (1982); and Fuerst, T. R. et al, *Mol. Cell. Biol.*, 7:2538–2544 (1987)). Vaccinia virus-based viral vectors which have been described include those which are useful as vaccines for hepatitis B (Smith, G. L. et al, *Nature*, 302:490–492 (1983); and Cheng, K. C. et al, *J. Virol.*, 61:1286–1290 (1987)); rabies (Kieny, M. P. et al, Nature, 312:163–166 (1984); and Wiktor, T. F. et al, *Proc. Natl. Acad. Sci.* USA, 81:7194–7198 (1984)); malaria (Smith, G. L. et al, *Science*, 224:397–399 (1984)): human respiratory syncytial virus (King, A. M. Q. et al, *J. Virol.*, 62:2885-2890 (1987)); human parainfluenza virus type 3 (Spriggs, M. K. et al, *J. Virol.*, 61:3416-3423 (1987)); rotavirus SA11 (Andrew M. E. et al, *J. Virol.*, 61:1054-1060 (1987)); influenza (Smith, G. L. et al, *Proc. Natl. Acad. Sci., USA*, 80:7155-7159 (1983); Smith, G. L. et al, *Virol.*, 160:336-345 (1987)); herpes simplex virus (Paoletti, E. et al, *Proc. Natl. Acad. Sci., USA*, 81:193-197 (1984); Gillespie, J. M. et al, *J. Clin. Microbiol.* 23:238-288 (1986); and Sullivan, V. et al, *J. Gen. Virol.*, 68:2587-2598 (1987)); vesicular stomatitis virus (Mackett, M. et al, *Science*, 227:433-435 (1985)); human immunodeficiency virus envelope proteins (Chakrabarti, S. et al, *Nature*, 320:535-537 (1986): Hu, S. L. et al, *Nature*, 320:537-540 (1986); and Hu, S. L. et al, *Nature*, 328:721-723 (1987)); and Friend murine leukemia virus envelope proteins (Earl, P. L. et al, *Science*, 234:728-731 (1986)). A vaccinia virus-based viral vector which expresses the coding gene sequences of the PRV g92 gene has also been described (European Patent Publication No. 0162738). In addition, vaccinia virus-based viral vectors which express host genes, such as murine interleukin-2 (Ramshaw, I. A. et al, *Nature*, 329:545-546 (1987)) and murine class I major histocompatibility complex antigen H-2Kd, have been reported (Coupar, B. E. H. et al, *Proc. Natl. Acad. Sci.*, USA, 83:7879-7882 (1986)).

Although there is evidence that genetically engineered vaccinia viruses have reduced pathogenicity, there are several major obstacles to their general use as vaccines. First, severe complications can occur after vaccination, especially in immunodeficient individuals. Second, they are highly infectious for many animal species and humans. The insertion of genes from heterologous virus species into vaccinia virus-based viral vectors could alter the recombinant vaccinia virus host range or tissue tropism. Therefore, as agents, vaccinia virus-based viral vectors pose potential health hazards. Third, there is no purpose served in vaccinating animals against smallpox, i.e., the disease that vaccinia protects against. Finally, potential recombination events between vaccinia virus and indigenous animal pox viruses might regenerate virulence of the vaccinia virus which will cause smallpox disease in humans.

Thus, in addition to herpes simplex virus and herpesvirus saimiri, other herpesviruses have been developed as species specific viral vectors for the species of animals which the viral vector infects. More specifically. PRV has been used as a viral-based vector for swine (U.S. patent application Ser. No. 857,703, filed Apr. 29, 1986; and PCT Publication No. 87/00157; and European Patent Publication No. 0256677). Further, IBRV has been used as a viral-based vector for cattle (U.S. patent application Ser. No. 07/148,725, filed Jan. 26, 1988 and PCT Publication No. 87/00157).

EHV-1-based viral vectors have distinct advantages over the above-discussed viral vectors for the vaccination of horses because they: (1) protect horses against the important equine disease of EHV-1; (2) are host-limiting e.g., they do not infect humans; and (3) are replication competent in horses.

However, prior to the present invention, it was not possible to develop EHV-1-based viral vectors because there were: (1) no recombinant EHV-1 viruses available, and (2) no knowledge of methods suitable for the construction of recombinant EHV-1 viruses.

In summary, the present invention provides for the first time: (1) methods which enable the introduction of genetic exchanges between the EHV-1 genome and exogenous DNA; (2) methods for isolating the rare EHV-1 recombinants from the recombination pool of EHV-1 viruses which contains an overwhelming proportion of parental EHV-1 and spontaneous mutants; (3) EHV-1 mutants with deletions in a non-essential EHV-1 gene: (4) EHV-1 mutants with insertions in a non-essential EHV-1 gene; and (5) EHV-1-based viral vectors which express foreign proteins. Thus, the present invention, for the first time demonstrates that EHV-1 can tolerate nucleotide sequence deletions and insertions of several kilobases.

Hence, the present invention provides, for the first time, not only a vaccine for EHV-1, but also as an EHV-1-based viral vector useful for expressing foreign proteins including but not limited to the genes for antigens of important pathogens of horses, such as Equine Arteritis Virus, Equine Infectious Anemia, Equine Encephalitis Viruses, and Equine Influenza.

SUMMARY OF THE INVENTION

An object of the present invention is to provide an EHV-1 vaccine effective in preventing EHV-1 disease symptoms and in controlling the spread of EHV-1 disease, and which can be safely administered to pregnant horses and foals.

Another object of the present invention is to provide an EHV-1 vaccine wherein the animal vaccinated with such is less likely to become a carrier of either the vaccine virus or a field virus.

A further object of the present invention is to provide a tk$^-$EHV-1 which cannot revert to tk$^+$ and is easily distinguished from tk$^+$EHV-1.

An even further object of the present invention is to provide an EHV-1 which has a deletion and/or insertion mutation in the tk gene and methods for the production thereof.

An additional object of the present invention is to provide an EHV-1 marker vaccine.

Another object of the present invention is to provide an EHV-1-based viral vector.

Still another object of the present invention is to provide an EHV-1 which can replicate efficiently at temperatures ranging from 30° C. to 40° C., i.e., inclusive of temperature-resistant viruses.

Yet another object of the present invention is to provide methods for genetically engineering EHV-1 recombinants.

Other objects of the present invention will be apparent from the detailed description of the invention provided hereinafter.

In one embodiment of the present invention, the above-described objects have been met by an EHV-1 which fails to produce any functional or antigenic non-essential EHV-1 gene product as a result of a deletion, an insertion or both a deletion and an insertion in a non-essential EHV-1 gene, and a vaccine for EHV-1 disease comprising:

(1) a pharmaceutically acceptable amount of said virus; and (2) a pharmaceutically acceptable carrier or diluent.

In another embodiment of the present invention, the EHV-1 is a temperature-resistant virus.

In still another embodiment of the present invention, the above-described objects have been met by a process for producing an EHV-1 which fails to produce any functional or antigenic non-essential EHV-1 gene product as a result of an insertion in a non-essential EHV-1 gene comprising:

(1) Constructing a hybrid plasmid comprising a cloning vector and a DNA fragment of EHV-1 containing substantially all of the non-essential EHV-1 gene and flanking sequences thereof;

(2) Inserting a foreign DNA sequence within the coding region of the non-essential EHV-1 gene of the hybrid plasmid of step (1);

(3) Co-transfecting, in semi-permissive immortalized EHV-1 host cells, the hybrid plasmid of step (2) with infectious DNA from a EHV-1 which expresses the non-essential EHV-1 gene product;

(4) Propagating the resulting EHV-1 of step (3) in permissive EHV-1 host cells;

(5) Selecting or screening for EHV-1 containing the foreign DNA sequence from the virus produced in step (4); and (6) Screening for EHV-1 which fails to produce any functional or antigenic non-essential EHV-1 gene product as a result of an insertion in the non-essential EHV-1 gene from the virus produced in step (5) so as to produce EHV-1 which fails to produce any functional or antigenic non-essential EHV-1 gene product as a result of an insertion in the non-essential EHV-1 gene.

In a further embodiment of the present invention, the above-described objects have been met by a process for producing an EHV-1 which fails to produce any functional or antigenic non-essential EHV-1 gene product as a result of a deletion in a non-essential EHV-1 gene comprising:

(1) Constructing a hybrid plasmid comprising a cloning vector and a DNA fragment of EHV-1 containing substantially all of the non-essential EHV-1 gene and flanking sequences thereof;

(2) deleting sequences within the coding region of the non-essential EHV-1 gene of the hybrid plasmid of step (1);

(3) Co-transfecting, in semi-permissive, immortalized EHV-1 host cells, the hybrid plasmid of step (2) with infectious DNA from an EHV-1 which fails to produce any functional or antigenic non-essential EHV-1 gene product as a result of an insertion of a foreign DNA sequence in the non-essential EHV-1 gene;

(4) Propagating the resulting EHV-1 of step (3) in permissive EHV-1 host cells;

(5) Selecting or screening for EHV-1 which do not contain the foreign DNA sequence insertion from the virus produced in step (4); and (6) Screening for EHV-1 which fails to produce any functional or antigenic non-essential EHV-1 gene product as a result of a deletion in the non-essential EHV-1 gene from the virus produced in step (5) so as to produce EHV-1 which fails to produce any functional or antigenic non-essential EHV-1 gene product as a result of a deletion in the non-essential EHV-1 gene.

In preferred embodiment of the process for producing the EHV-1 deletion mutant, the EHV-1 from which the infectious DNA in step (3) is obtained is an EHV-1-based viral vector and in step (5) screening is for EHV-1 which do not produce the gene product of the EHV-1-based viral vector.

In an additional embodiment of the present invention, the above-described objects have been met by an EHV-1-based viral vector comprising EHV-1 having inserted therein a foreign gene, other than an EHV-1 gene, adjacent to a functional gene promoter such that said foreign gene is expressed by said vector off of said functional gene promoter.

In another embodiment of the present invention, the above-described objects have been met by a EHV-1-based viral vector produced by the process comprising:

(1) Constructing a hybrid plasmid comprising a cloning vector and a DNA fragment of EHV-1 containing substantially all of a non-essential EHV-1 DNA sequence and flanking sequences thereof;

(2) Inserting a functional gene promoter and a foreign gene adjacent to said functional gene promoter within the non-essential EHV-1 DNA sequence of the hybrid plasmid of step (1) such that the expression of said foreign gene is controlled by said functional gene promoter and such that the resulting EHV-1 mutant of step (5) expresses said foreign gene;

(3) Co-transfecting, in semi-permissive, immortalized EHV-1 host cells, the hybrid plasmid of step (2) with infectious DNA from an EHV-1 such that homologous recombination between the infectious DNA and the plasmid of step (2) occurs through common DNA sequences flanking the insertion of the plasmid of step (2);

(4) Propagating the resulting EHV-1 of step (3) in permissive EHV-1 host cells; and (5) Selecting or screening for an EHV-1 mutant which expresses the gene product of said foreign gene, so as to produce an EHV-1-based viral vector which expresses said foreign gene.

In a preferred embodiment of the process for producing an EHV-1-based viral vector, there is an additional step which is carried out prior to or after step (5) comprising selecting or screening for an EHV-1 mutant which fails to produce the gene product of said non-essential EHV-1 DNA sequence such that the resulting EHV-1 mutant of the present invention also fails to produce the gene product of the non-essential EHV-1 DNA sequence.

BRIEF DESCRIPTION OF THE DRAWINGS

FIG. 3 illustrates the nucleotide sequence of a 1620 bp fragment which contains the coding region of the EHV-1 tk gene and flanking sequences thereof. This sequence is the complement of the DNA strand transcribed to produce EHV-1 TK mRNA. The translation start codon is at position 424 and the stop codon is at position 1480.

FIG. 4 schematically illustrates, by example, the derivation of pSVgpt(dl H-Bgl):BglII-BglII. This plasmid contains the SV40 early promoter adjacent to the E. coli gpt gene.

DETAILED DESCRIPTION OF THE INVENTION

Figure 1:
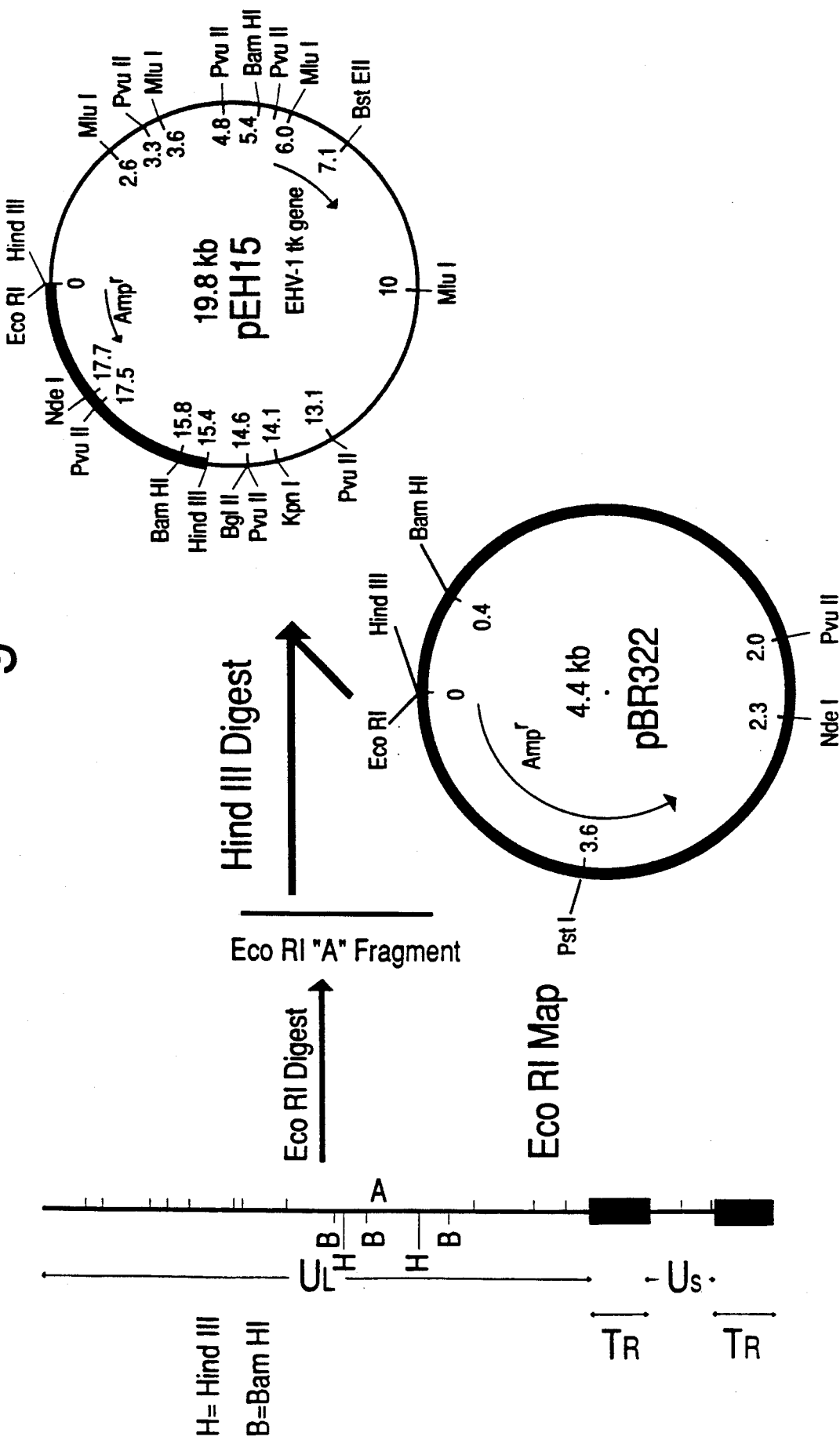
FIG. 1 schematically illustrates, by example, the derivation of pEH15 from the EcoRI "A" fragment of EHV-1 which contains the EHV-1 tk gene.

As described above, in one embodiment of the present invention, the above-described objects have been met by an EHV-1 which fails to produce any functional or antigenic non-essential EHV-1 gene product as a result of a deletion an insertion or both a deletion and an insertion in a non-essential EHV-1 gene, and a vaccine for EHV-1 disease comprising:

(1) a pharmaceutically acceptable amount of said virus; and (2) a pharmaceutically acceptable carrier or diluent.

In another embodiment of the present invention, the EHV-1 is a temperature-resistant virus.

In still another embodiment of the present invention, the above-described objects have been met by a process for producing an EHV-1 which fails to produce any functional or antigenic non-essential EHV-1 gene product as a result of an insertion in a non-essential EHV-1 gene comprising:

(1) Constructing a hybrid plasmid comprising a cloning vector and a DNA fragment of EHV-1 containing substantially all of the non-essential EHV-1 gene and flanking sequences thereof:

(2) Inserting a foreign DNA sequence within the coding region of the non-essential EHV-1 gene of the hybrid plasmid of step (1);

(3) Co-transfecting, in semi-permissive, immortalized EHV-1 host cells the hybrid plasmid of step (2) with infectious DNA from a EHV-1 which expresses the non-essential EHV-1 gene product;

(4) Propagating the resulting EHV-1 of step (3) in permissive EHV-1 host cells:

(5) Selecting or screening for EHV-1 containing the foreign DNA sequence from the virus produced in step (4); and (6) Screening for EHV-1 which fails to produce any functional or antigenic non-essential EHV-1 gene product as a result of an insertion in the non-essential EHV-1 gene from the virus produced in step (5) so as to produce EHV-1 which fails to produce any functional or antigenic non-essential EHV-1 gene product as a result of an insertion in the non-essential EHV-1 gene.

In a further embodiment of the present invention, the above-described objects have been met by a process for producing an EHV-1 which fails to produce any functional or antigenic non-essential EHV-1 gene product as a result of a deletion in a non-essential EHV-1 gene comprising:

(1) Constructing a hybrid plasmid comprising a cloning vector and a DNA fragment of EHV-1 containing substantially all of the non-essential EHV-1 gene and flanking sequences thereof:

(2) deleting sequences within the coding region of the non-essential EHV-1 gene of the hybrid plasmid of step (1):

(3) Co-transfecting, in semi-permissive, immortalized EHV-1 host cells, the hybrid plasmid of step (2) with infectious DNA from an EHV-1 which fails to produce any functional or antigenic non-essential EHV-1 gene product as a result of an insertion of a foreign DNA sequence in the non-essential EHV-1 gene;

(4) Propagating the resulting EHV-1 of step (3) in permissive EHV-1 host cells;

(5) Selecting or screening for EHV-1 which do not contain the foreign DNA sequence insertion from the virus produced in step (4); and (6) Screening for EHV-1 which fails to produce any functional or antigenic non-essential EHV-1 gene product as a result of a deletion in the non-essential EHV-1 gene from the virus produced in step (5) so as to produce EHV-1 which fails to produce any functional or antigenic non-essential EHV-1 gene product as a result of a deletion in the non-essential EHV-1 gene.

In preferred embodiment of the process for producing the EHV-1 deletion mutant, the EHV-1 from which the infectious DNA in step (3) is obtained is an EHV-1-based viral vector and in step (5) screening is for EHV-1 which do not produce the gene product of the EHV-1-based viral vector.

In an additional embodiment of the present invention, the above-described objects have been met by an EHV-1-based viral vector comprising EHV-1 having inserted therein a foreign gene, other than an EHV-1 gene, adjacent to a functional gene promoter such that said foreign gene is expressed by said vector off of said functional gene promoter.

In another embodiment of the present invention the above-described objects have been met by a EHV-1-based viral vector produced by the process comprising:

(1) Constructing a hybrid plasmid comprising a cloning vector and a DNA fragment of EHV-1 containing substantially all of a non-essential EHV-1 DNA sequence and flanking sequences thereof:

(2) Inserting a functional gene promoter and a foreign gene adjacent to said functional gene promoter within the non-essential EHV-1 DNA sequence of the hybrid plasmid of step (1) such that the expression of said foreign gene is controlled by said functional gene promoter and such that the resulting EHV-1 mutant of step (5) expresses said foreign gene;

(3) Co-transfecting, in semi-permissive, immortalized EHV-1 host cells the hybrid plasmid of step (2) with infectious DNA from an EHV-1 such that homologous recombination between the infectious DNA and the plasmid of step (2) occurs through common DNA sequences flanking the insertion of the plasmid of step (2);

(4) Propagating the resulting EHV-1 of step (3) in permissive EHV-1 host cells; and (5) Selecting or screening for an EHV-1 mutant which expresses the gene product of said foreign gene, so as to produce an EHV-1-based viral vector which expresses said foreign gene.

In a preferred embodiment of the process for producing an EHV-1-based viral vector, there is an additional step which is carried out prior to or after step (5) comprising selecting or screening for an EHV-1 mutant which fails to produce the gene product of said non-essential EHV-1 DNA sequence such that the resulting EHV-1 mutant of the present invention also fails to produce the gene product of the non-essential EHV-1 DNA sequence.

Non-essential EHV-1 genes, such as the EHV-1 tk gene, are approximately 1500 bp in size. The deletion mutants of the present invention can be produced by eliminating a 75 to 1500 bp DNA fragment from an appropriate coding region of the non-essential EHV-1 gene so that proper folding or substrate binding of the non-essential EHV-1 gene product, such as TK, is prevented. Alternatively, the deletion mutants can be produced by eliminating a 10 to 100 bp DNA fragment so that the proper reading frame of the non-essential EHV-1 gene is shifted. In the latter instance, a truncated polypeptide may be produced because polypeptide synthesis is aborted due to a frame shift-induced stop codon. The preferred size of the deletion is about 75 to 750 bp. Where the non-essential gene encodes an EHV-1 glycoprotein antigen, the deletion may be about 50 to 1500 bp so as to eliminate the nucleotide sequences encoding the principal epitopes of the antigen. The preferred deletion eliminates essentially all of the structural sequence of the non-essential gene encoding the EHV-1 glycoprotein antigen.

As discussed above, the deletion mutants can also contain a foreign DNA sequence in place of the deleted EHV-1 DNA such that hybrid RNAs are produced which are not processed, transported, or translated properly on the polyribosomes.

As used herein, a "foreign DNA sequence" means (1) any DNA sequence which does not encode a gene, i.e., a non-coding DNA sequence, regardless of origin, such as a viral, eucaryotic, or procaryotic non-coding sequence and inclusive of oligonucleotide linkers; (2) any DNA sequence which encodes a gene other than an EHV-1 gene and which is not an equivalent of the gene in which the insertion is made, e.g., if the insertion is in the EHV-1 tk gene, the DNA sequence may not be a viral, eucaryotic or procaryotic tk gene, or (3) any coding EHV-1 DNA sequence which has been translocated from its normal location on the EHV-1 genome to another location on the EHV-1 genome, such as the EHV-1 gp13 gene or the EHV-1 gp14 gene (Allen, G. P. et al, *J. Virol.* 61(8):2454–2461 (1987)) translocated into the EHV-1 tk gene.

As used herein, a "foreign gene" means (2) and (3) above for the definition of a "foreign DNA sequence". The preferred "foreign gene" is (2) above for the definition of a "foreign DNA sequence".

The size of the oligonucleotide linkers, whether used as an insertion alone or in combination with a deletion, is not critical to the present invention. Generally the size of the oligonucleotide linkers is 8–10 nucleotides in length, but can be longer, e.g., about 50 nucleotides or shorter e.g. 4, 5 or 7 nucleotides. The preferred length of the oligonucleotide linker is about 8 to 10 nucleotides in length. The DNA sequence of the oligonucleotide linker is also not critical to the present invention.

Similarly the size and sequences of other foreign DNA sequences employed in the present invention, as an insertion alone or in combination with a deletion, is not critical. Generally, the size of foreign DNA sequences, other than oligonucleotide linkers, is about 0.5 to 5 Kbp in length. For example, the (neo ®) gene and the *E. coli* lacZ gene, which can be employed as the foreign gene, are about 1.0 Kbp and 3.0 Kbp in length, respectively.

The particular site of deletion in the non-essential EHV-1 gene, such as the EHV-1 tk gene, is not critical. For example, in the EHV-1 tk gene the deletion can be made between the PvuI to BstEII restriction sites at 2.5 and 2.8 map units of pEP 3.7/IBI30, respectively. In addition, for example, in the EHV-1 gp13 gene, the deletion can be made from the NheI site at position 211 to the KpnI site at position 1331 (Allen, G. et al, *J. Virol.*, 62(8):2850–2858 (1988)). Alternatively the site of the deletion may be between new restriction sites which may be created anywhere in the non-essential EHV-1 gene by well known procedures, i.e., random or defined linker insertions, or through oligonucleotide mutagenisis (Heffron, F. et al, *Proc. Natl. Acad. Sci., USA,* 75:6012–6016 (1978); Strauss, M. et al, *Gene,* 49:331–340 (1986); Palmero, D. P. et al, *DNA,* 6:273–279 (1987); Sung, W. L. et al, *DNA,* 6:373–379 (1987); Kim, S. C. et al, *Science,* 240:504–506 (1988); and Su, T.-Z. et al, *Gene,* 69:81–89 (1988)). In EHV-1(dl TK) described below, a 0.4 kb deletion was introduced, by oligonucleotide mutagenisis, into the middle of the EHV-1 tk gene, spanning about 0.2 kb on either side of the BstEII restriction nuclease site at 2.5 map units on pEP 3.7/IBI30 (see FIG. 7).

The particular site of insertion into the non-essential EHV-1 gene, such as the EHV-1 tk gene, is also not critical. For example, in the EHV-1 tk gene, the insertion may be in the PvuI restriction nuclease site at 2.5 map units of pEP 3.7/IBI30. In addition, for example, in the EHV-1 gp13 gene, the insertion can be made at the NheI site at position 211 or the KpnI site at position 1331 (Allen, G. et al, *J. Virol.,* 62(8):2850–2858 (1988)). Alternatively, the site of the insertion may be between new restriction sites which may be created anywhere in the non-essential EHV-1 gene by well known procedures, i.e., random or defined linker insertions, or through oligonucleotide mutagenisis as discussed above. In EHV-1($\beta$-Gal) described below, the SV40 early promoter at the SV40 origin and the lacZ gene are inserted in the middle of the EHV-1 tk gene at the BglII restriction nuclease site at 5.8 map units of pEP 3.7(BstEII to BglII) (see FIG. 6). By the judicious choice of foreign DNA sequence length, frame shift mutations may be produced in the non-essential EHV-1 gene, augmenting the effect of insertions within the non-essential EHV-1 gene.

Similarly, in the EHV-1-based viral vector embodiment of the present invention the insertion site is not critical as long as the insertion site does not inactivate a gene required for viral replication, i.e., the insertion is within a non-essential EHV-1 DNA sequence. The tk⁻ EHV-1 insertion mutant expressing the *E. coli* lacZ gene described below, i.e., EHV-1($\beta$-Gal), is illustrative of the EHV-1-based viral vectors of the present invention.

The foreign gene which can be employed in the present invention is not critical thereto and can by the *E. coli* lacZ gene and the transposon Tn5 gene (neo ®) discussed above, in addition to complete or partial genes for antigens or antigenic portions thereof, of causative agents of infectious animal diseases such as equine encephalitis virus, Western equine encephalitis virus, Eastern equine encephalitis virus, Venezuelan equine encephalitis virus, St. Louis equine encephalitis virus, equine influenza virus, equine infectious anemia, equine arteritis virus, Potomac fever virus, and others.

Specific foreign genes which encode for proteins that elicit neutralizing antibodies and protection which can be employed in the present invention include Rabies G protein (Anilionis, A. et al, *Nature,* 294:275–278 (1981)); equine infectious anemia ENV protein gp70–gp45 (Rushlow, K. et al, *Virol.,* 155:309–321 (1986)); Eastern equine encephalitis virus E1 and E2 membrane proteins (Chang, G. J., et al, *J. Gen. Virol.,* 68:2129–2142 (1987)); Venezuelan equine encephalitis virus E1 and E2 membrane proteins (Kinney, R. M. et al, *Virol.,* 152:400–413 (1986)); and equine influenza virus hemagglutinin (Kawaoka, Y. et al, *Virol,* 169:283–292 (1989)).

The *E. coli* lacZ gene can be used as the foreign DNA sequence and can be fused to a functional gene promoter such that the resulting chimeric gene is flanked on both the 5' and 3' sides by, non-essential EHV-1 DNA, for example, EHV-1 tk DNA, in the tk−EHV-1 insertion mutants of the present invention, and in the EHV-1-based viral vectors of the present invention. This insertion mutant can then be screened for by assaying recombinant EHV-1 plaques expressing β-Galactosidase, which is detected by the blue color produced by action of the enzyme upon X-Gal (Boehringer-Mannheim) (Chakrabarti, S. et al, *Mol. Cell. Biol.*, 5:3403-3409 (1985)).

As discussed above, the transposon Tn5 gene (neo ®) can also be used as the foreign DNA sequence. This transposon encodes an aminoglycoside 3′-phosphotransferase and is capable of conferring resistance to neomycin and to the drug G418 (pNeo; Pharmacia P-L Biochemicals). To obtain expression of the transposon Tn5 gene, it is necessary that the functional gene promoter be positioned 5′ to the coding region of the transposon Tn5 gene. (Franke, C. A. et al, *Mol. Cell. Biol.*, 5:1918-1924 (1985)).

As used herein, the expression "functional gene promoter" means a DNA sequence capable of initiating RNA transcription from within the EHV-1 genome during EHV-1 infection.

The specific functional gene promoter employed in the present invention is not critical thereto and can include, for example, the EHV-1 tk gene promoter, the EHV-1 gp13 gene promoter (Allen, G. et al, *J. Virol.*, 62(8):2850-2858 (1988)); the EHV-1 gp14 gene promoter (Whalley, J. M. et al, *J. Gen. Virol.*, 70:383-394 (1989); promoters of other EHV-1 genes; or the SV40 early promoter.

The EHV-1 gp13 and EHV-1 gp14 gene promoters are the preferred EHV-1 gene promoters for three reasons. First, optimal gene expression during the lytic infection of the EHV-1 growth cycle occurs off of EHV-1 promoters. Cellular promoters and many other viral promoters are suppressed by EHV-1 factors which redirect mRNA synthesis solely towards the production of EHV-1 proteins. Second, the EHV-1 gp13 and EHV-1 gp14 gene promoters direct the abundant synthesis of mRNA.

Foreign DNA sequences inserted into the EHV-1 tk gene and other non-essential EHV-1 DNA sequence will only be expressed as a functional protein if the appropriate gene expression control signals are present. These signals consist of two types; those that control levels of mRNA and those that control efficiency of mRNA translation into protein.

The levels of mRNA are determined by transcription rates, mRNA processing efficiency and mRNA degradation rates. Relatively little is currently understood about the molecular control of the latter two parameters; however, the control signals which regulate transcription are better defined. Transcription, which is the process whereby mRNA is synthesized off a DNA template, occurs through interaction of RNA polymerase, and accessory protein factors with particular DNA sequences of the template. The sets of DNA sequences which bind RNA polymerase and control the site and onset of initiation of mRNA are collectively referred to as the promoter region.

The efficiency of translation of the mRNA is determined by the sequence and length of the leader mRNA fragment which precedes the start codon of the coding sequence; and by the presence of a short consensus sequence flanking the start codon called "Kozak's" sequence. There is great variation in the DNA sequences of promoters for different genes from a variety of species. Even within the herpesvirus genome, there are few if any recognizable common features within the DNA sequences of different viral gene promoters. Detailed functional studies of several eucaryotic promoters have demonstrated the common occurrence of canonical consensus sequences, the TATA site which determines the point of initiation of the mRNA, and the CAAT box, which effects transcription efficiency. In addition, there are upstream distal signals which further modulate transcription efficiencies.

Foreign DNA sequences containing coding open reading frames that are inserted into, for example, the EHV-1 tk gene may be expressed as fusion proteins off of the EHV-1 tk gene promoter if the inserted coding sequence is in phase with the EHV-1 tk gene coding sequence, and if no stop codons are interposed. However, insertion mutants of this type are not preferred because the EHV-1 tk gene promoter is "weak", producing low levels of mRNA; and because fusion proteins are often less immunogenic than native forms.

In addition, production of mRNA employs the presence of transcription termination and polyadenylation signals. Eucaryotic transcription termination signals are at present poorly defined. However, polyadenylation signals are known to contain the consensus sequence "AATAAA". The EHV-1-based viral vectors of the invention can utilize the polyadenylation and downstream transcription termination signals of the non-essential EHV-1 gene adjacent to the insert; thereby assuring correct termination and polyadenylation of the mRNA of the inserted foreign DNA; or the polyadenylation and downstream transcription signals and splice regions of SV40 present in the pEP 3.7/SV2β-gal.

If the insertion is a non-coding DNA sequence, the desired recombinant EHV-1 may be identified by hybridization of a labelled probe derived from the non-coding DNA sequence or by polymerase chain reaction methods.

The viruses of the present invention which express complete or partial genes for antigens or antigenic portions thereof as foreign genes can be screened for by standard immunological procedures. A convenient and rapid procedure for identifying plaques formed by viruses expressing such foreign genes is well known (Holland, T. C. et al, *J. Virol.*, 46:649-652 (1983)). In addition, the viruses of the present invention which express foreign antigens can be screened for by co-expression of a marker gene, such as the lacZ gene (Chakrabarti, S. et al, *Mol. Cell. Biol.*, 5:3403-3409 (1985)).

In the process for producing a EHV-1-based viral vector and in the preferred embodiment of the EHV-1 non-essential EHV-1 gene- EHV-1 insertion mutant, i.e., wherein a foreign gene is inserted in the non-essential EHV-1 gene, "selection means" or "screening means" can be employed. Whether "selection means" or "screening means" is employed will depend on the non-essential EHV-1 DNA sequence within which the insertion is made. For example, if the non-essential EHV-1 DNA sequence encodes a non-essential gene which is an antigen such as EHV-1 gp13, "screening means" are employed. On the other hand, if the non-essential EHV-1 DNA sequence within which the insertion is made is a dominant marker, for example, a tk gene (an EHV-1 tk gene or other viral, eucaryotic or procaryotic tk gene) or the (neo ®) gene, "selection means" are employed. In addition, whether "selection means" or "screening means" is employed will depend upon the foreign gene used as the insertion. For example, if the foreign gene to be inserted is, e.g., the lacZ gene or an antigen gene, "screening means" will be employed. On the other hand, if the foreign gene is a dominant marker, "selection means" will be employed.

"Screening" means which do not utilize an EHV-1 gene as the marker, or "selection" means which do not utilize an EHV-1 gene as the selectable marker are preferred because there will not be a high background of spontaneous mutants or revertants which will obscure the identification of the desired recombinant EHV-1.

As used herein, "selection means" refers to the enrichment of the fraction of a desired recombinant virus in the total virus population. Further, as used herein "screening means" refers to the identification of the desired recombinant within the total virus population.

Selection means are preferred when used alone, or prior to screening means, when used in combination therewith. This is because the resulting enrichment for the desired recombinant viruses due to the use of selection means reduces the amount of screening required to obtain the recombinant viruses.

As discussed above, in the selection means, a dominant marker such as the (neo®) gene, may be employed to select for recombinant viruses with insertions in any non-essential EHV-1 DNA sequence, regardless of whether the parental EHV-1 expresses the non-essential gene product, e.g., regardless of whether the parental EHV-1 is $tk^+$or $tk^-$. On the other hand, when the dominant marker is a tk gene, only $tk^-$parental EHV-1 may be employed since such allows for selection of $Tk^+$EHV-1.

Thus, in the present invention it is also possible to select or screen for the gene product produced by the foreign gene insertion so as to obtain non-essential gene-EHV-1 insertion mutants and EHV-1-based viral vectors which express the foreign gene.

As used herein, a "non-essential EHV-1 DNA sequence" means a region of the EHV-1 genome which is not required for viral replication, i.e., a non-essential EHV-1 gene or a non-coding region of the EHV-1 genome. The preferred non-essential EHV-1 DNA sequence is a non-essential EHV-1 gene.

The non-essential EHV-1 DNA sequence employed in the present invention is not critical thereto.

Examples of such non-essential EHV-1 DNA sequence include the EHV-1 tk gene discussed above, the EHV-1 gp13 gene, and other EHV-1 genes corresponding to the gX and gI genes of PRV. The preferred non-essential EHV-1 gene is the EHV-1 tk gene because $tk^-$mutants are attenuated and preferred as vaccines.

As used herein, "flanking sequences" means the sequences upstream, downstream, or both upstream and downstream, from the non-essential EHV-1 DNA sequence. e.g.. the EHV-1 tk gene coding sequences. The upstream sequences for the non-essential EHV-1 gene contain the transcriptional control signals, i.e., promoters and enhancers, whereas the downstream sequences contain the transcription termination and polyadenylation signal of, for example, the EHV-1 tk gene.

The method of inserting the foreign DNA sequence into plasmid DNA will depend upon the type of foreign DNA sequence used and/or the sequence of the gene in which it is to be inserted. Palindromic double stranded linkers containing one or more restriction nuclease sites in the oligonucleotide sequence (New England Biolabs, Inc.) may be inserted by well known procedures (Maniatis, T. et al, *Molecular Cloning* Cold Spring Harbor Laboratory (1982)). Foreign DNA sequences may also be inserted into plasmid DNA by tailing ends with complementary homopolymers using terminal transferase (Maniatis, T. et al, *Molecular Cloning*, Cold Spring Harbor Laboratory (1982)).

The particular cloning vector employed in the present invention to construct the hybrid plasmid comprising a DNA fragment of EHV-1 containing substantially all of the non-essential EHV-1 DNA sequence, e.g., the EHV-1 tk gene, and flanking sequences thereof of step (1) is not critical as long as the cloning vector contains a gene coding for a selective trait, e.g., drug resistance. Examples of such cloning vectors include pBR322 and pBR322-based vectors (Sekiguchi, T. et al, *Gene*, 21:267-272 (1983)), pMB9, pBR325, pKH47 (Bethesda Research Laboratories), pBR328, pHC79 (Boehringer-Manneheim Biochemicals), phage Charon 28 (Bethesda Research Laboratories) pKB11, pKSV-10 (P-L Biochemicals), pMAR420 (Otsuka H. et al, *Virol.* 113:196-213 (1981)) and oligo (dG)-tailed pBR322 (New England Nuclear)).

pBR322 is a preferred cloning vector employed in the examples of the present invention since the EHV-1 3.7 kb PstI fragment was found to contain the EHV-1 tk gene and pBR322 only has one PstI cloning site (see FIG. 1). Insertion of a DNA fragment at this site inactivates the cloning vector's ampicillin gene, but not the tetracycline gene, so that ampicillin-sensitive, tetracylcine-resistant hybrid plasmids that are larger than pBR322 due to the insertion can easily be isolated. The preferred cloning vector for other non-essential EHV-1 genes would be apparent to one skilled in the art upon examination of available cloning sites and restriction nuclease sites flanking the non-essential EHV-1 gene.

It has also been found that the a 15 kb HindIII fragment contains the EHV-1 tk gene (see FIG. 1). Thus, pBR322, pUC18, pBR328, pBR325 and other cloning vectors containing a single HindIII site are useful cloning vectors for cloning the EHV-1 tk gene.

The specific host employed for growing the hybrid plasmids of the present invention is not critical to the present invention. Examples of such hosts include *E. coli* K12 RR1 (Bolivar F. et al, *Gene*, 2:95-113 (1977)); *E. coli* K12 HB101 (ATCC No. 33694); *E. coli* MM21 (ATCC No. 336780); and *E. coli* DH1 (ATCC No. 33849). *E. coli* K12 RR1 is the preferred host and has an $F^-$hsd R hsd M genotype.

Similarly, alternative vector/cloning systems can be employed such as plasmid vectors which grow in *E. coli* or *Saccharomyces cerevisiae*, or both, or plasmid vectors which grow in *B. subtilus*, or even vectors such as bovine papilloma virus (ATCC No. 37112) which grow in animal cells such as mouse (ATCC No. RL1616) (Elder, J. T. et al, *Ann. Rev. Gen.*, 15:295-340 (1981) and Ure, R. et al, *Methods in Enzymology* "Recombinant DNA" Vol. 101, Part C, Academic Press, N.Y. (1983)).

The precise non-essential EHV-1 gene, e.g., EHV-1 tk gene, sequences which must be present in the hybrid plasmids of steps (1) and (3) of the present invention will depend on the sequences chosen to be inserted and/or deleted, and the restriction nucleases to be employed in the engineering of the insertion and/or deletion mutant.

The specific EHV-1 DNA sequences adjacent to the insertion and/or deletion required in the hybrid plasmid in steps (1) and (3) of the present invention will depend on the specifics of the insertion and/or deletion in the hybrid plasmid. In general, the size of the EHV-1 DNA sequences adjacent to both the 3' and 5' sides of the insertion and/or deletion will be at least about 400 bp. In pEP 3.7/SV2β-gal (see FIG. 6), described in detail below, the 3' and 5' sequences on both sides of the insertion were 1.5 Kbp and 2.2 Kbp in length, respectively. Similarly in pEP 3.7/IBI30 dl TK (see FIG. 7). described in detail below the 3' and 5' sequences on both sides of the deletion were 1.3 Kbp and 2.0 Kbp in length, respectively.

The specific EHV-1 strain which expresses the non-essential gene product employed as a starting material in the present invention from which the EHV-1 DNA fragment containing the non-essential EHV-1 DNA sequence, e.g., the EHV-1 tk gene, of step (1) and the infectious EHV-1 DNA of step (3) of the EHV-1 insertion mutant embodiment of the present invention are obtained is not critical. Similarly, the specific EHV-1 strain which expresses the non-essential gene product employed as a starting material for the EHV-1-based viral vector is not critical to the present invention. These EHV-1 strains may be either non-temperature resistant or temperature resistant. Examples of such strains include the well-known attenuated strains such as the L-M cell adapted Kentucky A strain (Randall, C. C. et al, *Proc. Soc. Exp. Biol. Med.*, 110:487-489 (1962)). the hamster adapted Kentucky A strain (Randall, C. C. et al, *Amer. J. Pathol.*, 33:709-727 (1957)); Rhinoquin TM strain (Phillips Roxane); and the Rhinoimmune TM strain (Norden Laboratories, Inc.); and virulent strains isolated directly from diseased animals or passaged frequently in the laboratory, such as the Army 183, Q, MS, Kentucky B and Kentucky D strains (Studdert, M. J. et al, *Arch. Virol.*, 77:249-258 (1983); and McCullum, W. H. et al, *Am. J. Vet. Res.*, 17:267-270 (1956)).

If the insertion and/or deletion is to be made in a non-essential EHV-1 sequence other than the EHV-1 tk gene it is preferable that the EHV-1 strain employed for recombination be an attenuated strain so that the resulting insertion mutant possesses the attenuated properties of the attenuated strain. An attenuated strain is the preferred EHV-1 strain which expresses the non-essential EHV-1 gene product from which the EHV-1 DNA fragment containing the EHV-1 non-essential gene of step (1) is derived and is the preferred EHV-1 which expresses the non-essential EHV-1 gene product from which the infectious EHV-1 DNA of step (3) is derived from the EHV-1 insertion mutant embodiment of the present invention.

tk−EHV-1 strains can also be employed as a starting material for the production of the EHV-1 deletion mutants and EHV-1-based viral vectors of the present invention. These EHV-1 strains may also be either non-temperature resistant or temperature resistant. The specific tk−EHV-1 strain employed as a starting material in the EHV-1 deletion embodiment of the present invention is not critical thereto but, preferably contains a marker, such as found in, for example, EHV-1(β-Gal), described in detail below. The specific tk−EHV-1 strain employed as a staring material in the EHV-1-based viral vector embodiment of the present invention is also not critical to the present invention and includes EHV-1(β-Gal) or the mutagen-induced tk−Kentucky A strain (Allen G. P. et al, *Virol.*, 90:351-359 (1978)). EHV-1(β-Gal) is the preferred tk−EHV-1 strain employed as the starting material for the production of the EHV-1 deletion mutants of the present invention because it expresses the β-gal gene and allows efficient selection means to be employed. EHV-1(β-Gal) is also the preferred tk−EHV-1 strain employed as the starting material for the production of the EHV-1-based viral vector of the present invention because, as discussed above, it expresses the β-gal gene and allows efficient selection means to be employed.

In co-transfecting step (3) of the present invention, either tk+ or tk− semi-permissive immortalized EHV-1 host cells can be employed, although tk+EHV-1 semi-permissive, immortalized host cells are preferred because the desired tk− recombinant virus grow more efficiently in tk+ semi-permissive EHV-1 host cells.

Semi-permissive, immortalized EHV-1 host cells are employed so as to increase infectivity and the recombination rate in co-transfecting step (3).

The specific semi-permissive, immortalized EHV-1 host cells employed in the present invention in co-transfecting step (3) are not critical thereto and depends upon the EHV-1 strain employed in step (3). Examples of such semi-permissive EHV-1 host cells include RAB-9 (rabbit skin cells) (ATCC No. 1414) and RAB(BU) (Kit, S. et al, *J. Med. Virol.*, 12:25-36 (1983)). RAB-9 are the preferred semi-permissive, immortalized EHV-1 host cells employed in the present invention for co-transfecting step (3). This is because the EHV-1 strain employed in the examples herein, i.e. the Rhinoquin TM strain, has not been cell-adapted for growth in rabbit cells. If the EHV-1 strain employed in co-transfecting step (3) is adapted to a non-equine cell line, then this cell line would not be semi-permissive host cells for such an EHV-1 strain. For example, L-M cells are permissive EHV-1 host cells for the L-M adapted Kentucky A strain (Randall, C. C. et al, *Proc. Soc. Exp. Biol. Med.*, 110:487-489 (1962)). whereas L-M cells are semi-permissive host cells for the parental Kentucky A strain.

On the other hand, for propagating the viruses in step (4) of the present invention, permissive EHV-1 host cells are employed in the present invention.

The particular permissive EHV-1 host cells employed in the present invention will depend on the virus strain. That is, to select for a functional neo ® gene or lacZ gene, either tk+ or tk− permissive EHV-1 host cells can be employed since neither naturally produce the neo ® or lacZ gene products. To select for other foreign genes, either tk+ or tk−EHV-1 permissive host cells can also be employed with the only limitation being that the host cells employed do not produce the gene product of the inserted foreign gene.

The specific permissive EHV-1 host cells employed in the present invention for propagating the viruses of the present invention are not critical thereto. Examples of such permissive EHV-1 host cells include Vero cells (ATCC No. CCL-81); BHK-21 cells (Whalley, J. M. et al, *J. Gen. Virol.*, 70:383-394 (1989)); equine dermal cells (Turtinen, L. W. et al, *Am. J. Vet. Res.*, 42:2099-2104 (1981)); equine dermis (NBL-6) cells (ATCC No. CCL-57); and equine kidney cells (ATCC No. CRL-6289). Vero cells are the preferred permissive EHV-1 host cells employed in step (4) of the present invention for propagating the viruses of the present invention. This is because the EHV-1 strain employed in the examples herein, i.e., the Rhinoquin TM strain, is Vero cell-adapted for growth. If the EHV-1 strain employed in step (4) is adapted to another permissive EHV-1 cell line, this adapted cell line would be preferred. For example, L-M cells are employed as the permissive EHV-1 cells for the L-M cell adapted Kentucky A strain (Randall, C. C. et al, *Proc. Soc. Exp. Biol. Med.*, 110:487–489 (1962)) and hamster cells are employed as the permissive EHV-1 cells for the hamster adapted Kentucky A strain (Randall, C. C. et al, *Amer. J. Pathol.*, 33:709–727 (1957)). In the case of a non-adapted EHV-1 strain, the preferred permissive EHV-1 host cells of step (4) are of equine origin. However, it should be noted that for the production of virus to be used for vaccination of animals in the field, a United States Department of Agriculture certified cell line permissive for EHV-1, preferably of the same species as the animal to be vaccinated, and free of other infectious agents, should be used. For example, a suitable equine cell would be certified diploid non-tumorgenic fetal equine kidney cells free of mycoplasma and other viruses.

In the context of this invention, a temperature-resistant virus is a virus which is non-temperature sensitive. Thus, a temperature-resistant virus is capable of replicating, at a non-permissive temperature, i.e., about 38.5° C. to 40° C., preferably 39.1° C., about as well as the parental virus or field isolates of EHV-1 replicate at a permissive temperature. By contrast, temperature-sensitive EHV-1 strains contain mutations in viral genes essential for replication, whereby functional gene products are produced at permissive temperatures, i.e., about 32° C. to 37.5° C., preferably 34.5° C., but not at non-permissive temperatures. Therefore, in temperature-sensitive viruses, production of infectious virus particles is 4 to 7 logs lower at the non-permissive temperatures compared to production at permissive temperatures. With temperature-resistant virus strains, production of infectious virus particles is about the same at non-permissive temperatures as at permissive temperatures.

To obtain temperature-resistant equine herpesvirus type 1 mutants, the infectious DNA of step (3) is derived from a temperature-resistant equine herpesvirus type 1 such that the resulting mutants of step (3) are temperature-resistant equine herpesvirus type 1 mutants or there is an additional step comprising propagating the resulting equine herpesvirus type 1 mutants at a non-permissive temperature for a temperature-sensitive virus so as to select for and produce temperature-resistant equine herpesvirus type 1 mutants.

Temperature-resistant viruses are superior to temperature-sensitive viruses as modified-live virus vaccines because (1) attenuation results from alterations in pathogenic viral genes rather than from crippling viral genes required for replication; and (2) temperature-resistant viruses can be safely administered intramuscularly, intranasally or intravenously and can replicate in the deep tissues of the body so as to elicit a more complete and prolonged immunological response.

In contrast, temperature-sensitive viruses only replicate at low temperature sites such as the upper respiratory tract, and thus, can only be administered intranasally.

The EHV-1 mutants of the present invention can be employed as modified-live virus vaccines against equine diseases alone or when containing additional mutations which attenuate EHV-1. Such additional mutations include a deletion in the US region.

Alternatively, the EHV-1 mutants of the present invention can be employed as killed virus vaccines against equine disease. That is, inactivation of infectivity by ultraviolet light or formaldehyde treatment of, e.g., the tk−EHV-1 mutants, yields a vaccine capable, after intraperitoneal administration, of eliciting cytotoxic T cells and protective antibodies against surface glycoproteins of EHV-1 or of foreign genes present in EHV-1-based viral vectors. Animals immunized with this vaccine would thus be protected against virulent virus infections.

Furthermore, non-ionic detergent extracts (Nonidet P40 or Triton X-100) can be made from EHV-1 mutant-infected equine cells to produce subunit EHV-1 vaccines. After purification of the glycoproteins, they can be employed as subunit vaccines (Hilleman, M. R. et al, In: *The Human Herpesvirus: An Interdisciplinary Perspective*, Eds. Nahmias, A. J. et al, (Elsevier, New York), page 503 (1981); Eisenberg, R. J. et al, *J. Virol.*, 41:1099–1104 (1982); Long, D. et al, *Infec. Immun.*, 37:761–764 (1984); and Dix, R. D. et al, *J. Med. Virol.*, 17:9–18 (1985)).

A pharmaceutically effective amount of the EHV-1 mutants of the present invention can be employed along with a pharmaceutically acceptable carrier or diluent as a vaccine against equine disease in animals, such as horses, mules, donkeys burros and zebras.

Examples of pharmaceutically acceptable carriers or diluents useful in the present invention include any physiological buffered medium, i.e., about pH 7.0 to 7.4, containing from about 2.5 to 15% (v/v) serum which does not contain antibodies to EHV-1, i.e., is seronegative for EHV-1. Agammaglobulin serum is preferred to serum which contains gammaglobulin. Examples of serum to be employed in the present invention include: swine serum, calf serum, fetal calf serum, horse serum and lamb serum. Agammaglobulin horse serum from equine seronegative for EHV-1 would be preferred for vaccination of equine. Equine protein, such as equine albumin, or bovine serum albumin in an amount of from about 0.5 to 3.0 (w/v%) can be employed as a substitute for serum. However, it is desirable to avoid the use of foreign proteins in the carrier or diluent which will induce allergic responses in the animal being vaccinated. Prior to lyopholization, the virus may be diluted using any of the conventional stabilizing solutions containing phosphate buffered saline, glutamate, casitone or lactose hydrolyzate, sucrose, sorbose, lactose, gelatin and preservatives such as gentamicin, fungazone and amphotericin B.

It is preferred that the viruses of the present invention be stored at a titer of at least $10^{5.5}$ to $10^{6.5}$ p.f.u./ml in a lyopholized state at 4° C. to −20° C. The lyopholized virus may be reconstituted for use with sterile distilled water containing 1.0% (v/v) glycerol.

The useful dosage of the vaccine to be administered will vary depending upon the age, weight and species of the animal vaccinated and the mode of administration. As a live modified virus vaccine, a suitable dosage can be, for example, about $10^{4.5}$ to $10^{6.5}$ p.f.u., preferably about $10^{5.0}$ to $10^{6.0}$ p.f.u. As a killed vaccine, a suitable dosage can be, for example, about 10 to 100 fold greater than that employed for a modified-live virus vaccine, including an appropriate adjuvant.

The vaccines of the present invention can be administered intramuscularly and subcutaneously. Intramuscularly is the preferred mode of administration. The modified-live vaccines of the present invention can also be administered intranasally.

The following examples are provided for illustrative purposes only and are in no way intended to limit the scope of the present invention.

In the following examples, all media and buffer solutions were made in glass distilled water unless otherwise indicated.

EXAMPLE 1

Production of tk⁻Insertion Mutants of EHV-1

A. Origin of EHV-1 Strains

The EHV-1 strain used in this example was the well-known Rhinoquin™ vaccine strain manufactured by Philips Roxane, Inc., St. Joseph, Mo. (Purdy, C. W. et al, *Am. J. Vet. Res.*, 38(8):1211–1215 (1977); and U.S. Pat. No. 4,110,433). However any other tk+strain of EHV-1 could be employed herein without departing from the spirit and scope of the present invention. The EHV-1 strain employed in this example had originally been attenuated by 13 passages in Vero cells at 37° C. and 50 passages in Vero cells at 26° C. Although the strain was attenuated in horses compared to field isolates of EHV-1, this strain was found, after large scale use of the vaccine and after U.S.D.A. licensure to occasionally cause neurological symptoms resulting in the withdrawal of the vaccine from the market.

B. Preparation of Virus Pools and EHV-1 DNA

EHV-1 was propagated in Vero cells (ATCC No. CCL-81) and titrated in Vero cells as described for PRV and IBRV in U.S. Pat. No. 4,514,497 and U.S. Pat. No. 4,703,011, respectively, which are incorporated by reference herein in their entirety. EHV-1 DNA was prepared by infection of Vero cells as described by Pignatti, P. F. et al, *Virol.*, 93:260–264 (1979) for the preparation of HSV DNA, and as described in more detail in U.S. Pat. No. 4,514,497 and U.S. Pat. No. 4,703,011 for PRV DNA and IBRV DNA, respectively, with the exception that EHV-1 DNA was found in a less dense fraction of CsCl equilibrium gradients compared to that found for PRV DNA or IBRV DNA. This is because EHV-1 DNA has a lower (G+C)% content than PRV DNA or IBRV DNA. Specifically, EHV-1 DNA was found at a density of 1.716 gm/ml. EHV-1 DNA was characterized by the pattern of restriction nuclease digestion fragments on agarose gels electrophoresis as described in U.S. Pat. No. 4,514,497 and U.S. Pat. No. 4,703,011.

C. Cloning of EHV-1 DNA

The genomes of the alpha-herpesviruses HSV-1, HSV-2, PRV, and EHV-1 have been found to have regions of homology and colinearity (Davison, A. J. et al, *J. Gen. Virol.*, 64:1927–1942 (1983)). The genomic location of the PRV tk gene corresponds to a general region on the EHV-1 genome covered by a 40 kb EcoRI fragment representing ⅓ of the $U_L$ segment of the genome (see FIG. 1). Therefore, it was postulated in the present invention that this fragment could be used to locate the EHV-1 tk gene.

The EHV-1 EcoRI 40 kb DNA fragment was obtained as follows.

5.0 μg of EHV-1 DNA was dissolved in 250 μl of a buffer comprising 50 mM NaCl, 100 mM Tris-HCl (pH 7.5), 5.0 mM $MgCl_2$, and 100 μg/ml of bovine serum albumin (hereinafter "BSA") (hereinafter "EcoRI cutting buffer"). The DNA was then digested at 37° C. for 1 hour with 20 units of EcoRI (New England Biolabs). Then, the reaction was terminated by adding a 1/5th volume of 0.1M cyclohexanediamine tetraacetate (hereinafter "CDTA") and heating at 65° C. for 30 minutes. Next, the DNA was loaded upon a 10–40% (w/v) sucrose gradient in buffer comprising 10 mM Tris-HCl (pH 7.5), 1.0 mM EDTA, and 50 mM NaCl, and centrifuged in a SW41 rotor (Beckman Instruments) at 28,000 rpm, at 4° C. for 28 hours. Then, fractions were collected, and aliquots of the fractions analyzed on agarose gels as described in U.S. Pat. No. 4,514,497. Next, the fraction containing the 40 kb EcoRI fragment was mixed with 2.0 μg of carrier yeast tRNA and a 1/10th volume of 3.0M sodium acetate (pH 7.5). The DNA was precipitated by adding 2 volumes of ethanol and storing at −20° C. overnight. The resulting 40 kb DNA precipitate was collected by centrifugation and dissolved in 0.1×TE buffer. TE buffer comprises 10 mM Tris-HCl (pH 7.5) and 1.0 mM EDTA.

To clone the BamHI fragments within the resulting 40 kb EHV-1 EcoRI fragment, the 40 kb DNA fragment was dissolved in 50 μl of a buffer comprising 150 mM NaCl, 6.0 mM Tris-HCl (pH 7.9), 6.0 mM $MgCl_2$, 6.0 mM 2-mercaptoethanol, and 100 μg/ml of BSA (hereinafter "BamHI cutting buffer") and digested with 20 units of BamHI (New England Biolabs) for 1 hour at 37° C. Then, the reaction was terminated by adding a 1/5th volume of 0.1M CDTA and a 1/20th volume of 3.0M sodium acetate (pH 7.5) and heating at 65° C. for 30 minutes.

The resulting BamHI-digested DNA was mixed with 0.1 μg of BamHI-digested, dephosphorylated pBR322 (New England Biolabs), dissolved in 0.05 ml of a buffer comprising 50 mM Tris-HCl (pH 7.8), 10 mM $MgCl_2$, 20 mM dithiothreitol, 1.0 mM ATP, and 50 μg/ml of BSA (hereinafter "ligation buffer"), containing about 1000 units of phage T4 DNA ligase (New England Biolabs), and incubated overnight at 4° C. Then, the reaction was terminated by adding EDTA to 20 mM. and heating at 65° C. for 10 minutes.

The resulting recombinant plasmids DNA were diluted in TE buffer and used to transform *E. coli* K12 RR1 bacteria as described in U.S. Pat. No. 4,514,497. Thereafter, rapid screening of the resulting clones for the desired recombinant plasmids was conducted as described in U.S. Pat. No. 4,514,497. Large scale purification of plasmid DNA was performed as described in U.S. Pat. No. 4,514,497, or by a standard modification in which the DNA was purified on CsCl-ethidium bromide equilibrium gradients (Maniatis, T. et al, *Molecular Cloning*, Cold Spring Harbor Laboratory (1982)).

In the above manner, recombinant plasmid pEB15 which contained the 15 kb EHV-1 BamHI fragment cloned from the 40 kb EHV-1 EcoRI fragment, was isolated.

To clone the HindIII fragments within the resulting 40 kb EHV-1 EcoRI fragment the 40 kb DNA fragment was dissolved in 50 μl of a buffer comprising 50 mM NaCl, 50 mM Tris-HCl (pH 8.0), 10 mM $MgCl_2$, and 100 μg/ml of BSA (hereinafter "HindIII cutting buffer") and digested with 20 units of HindIII (New England Biolabs) for 1 hour at 37° C. Then, the reaction was terminated by adding a 1/5th volume of 0.1M CDTA and a 1/20th volume of 3.0M sodium acetate (pH 7.5), and heating at 65° C. for 30 minutes.

The resulting HindIII-digested DNA was mixed with 0.1 μg of HindIII-digested, dephosphorylated pBR322, dissolved in 0.05 ml of ligation buffer containing about 1000 units of phage T4 DNA ligase, and incubated overnight at 4° C. Then, the reaction was terminated by adding EDTA to 20 mM. and heating at 65° C. for 10 minutes.

The resulting recombinant plasmids DNA were diluted in TE buffer and used to transform *E. coli* K12 RR1 bacteria as described in U.S. Pat. No. 4,514,497. Thereafter, rapid screening of the resulting clones for the desired recombinant plasmids was conducted as described in U.S. Pat. No. 4,514,497. Large scale purification of plasmid DNA was performed as described in U.S. Pat. No. 4,514,497, or by a standard modification in which the DNA was purified on CsCl-ethidium bromide equilibrium gradients (Maniatis, T. et al, "Molecular Cloning", Cold Spring Harbor Laboratory (1982)).

In the above manner, recombinant plasmid pEH15, which contained the 15 kb EHV-1 HindIII fragment cloned from the 40 kb EHV-1 EcoRI fragment, was isolated (see FIG. 1).

D. Identification of a Fragment Encoding the EHV-1 tk Gene by a Transient Expression Assay In order to identify fragments encoding the EHV-1 tk gene, the following transient expression RAB(BU) cells, a tk⁻ rabbit cell line obtained as described in Kit, S. et al, *J. Med. Virol.*, 12:25–36 (1983), were transfected with calcium phosphate DNA precipitates (Graham, F. L. et al, *Virol.*, 52:456–467 (1973)). Specifically, the following sterile solutions were added to a test tube in sequential order:

(1) 0.26 ml of a 10 μg/ml solution in 0.1×TE buffer of a recombinant plasmid containing EHV-1 DNA fragments;

(2) 0.10 ml of a 100 μg/ml solution of carrier mouse fibroblast (LM(TK⁻)) cell DNA in TE buffer;

(3) 0.05 ml of 2.0M CaCl$_2$ and (4) 0.4 ml of a 2×balanced salt solution comprising 280 mM NaCl 1.5 mM Na$_2$HPO$_4$, and 50 mM Hepes (pH 7.12) (hereinafter "2×BSS").

The resulting solution was mixed and kept at room temperature for 30 minutes while a DNA-calcium phosphate precipitate formed. Then, 0.04 ml of the suspension containing the DNA-calcium phosphate precipitate was added directly to 0.35 ml of growth medium covering RAB(BU) cells which had been seeded into 8 well Lab-Tek ™ slides (Miles Laboratories) 36 hours earlier. The media was changed immediately prior to transfection to growth media supplemented with 100 μM chloroquine. Inclusion of chloroquine increases the proportion of cells which take up the exogenous plasmid DNA (Luthman, H. et al, *Nuc. Acids Res.*, 11(5):1295–1308 (1983)). Then, the transfected cells were incubated at 37° C. for 4 hours, the medium was aspirated and replaced with growth medium alone. After 36 hours of incubation at 37° C., the medium was replaced with APMEM plus 10% (v/v) fetal bovine serum containing 0.1 μg/ml of cold thymidine and 5.0 μCi/ml of ³H-thymidine. After another 24 hours of incubation at 37° C., the medium was aspirated, and the cells rinsed with 1×GKN (U.S. Pat. No. 4,514,497). Then, the cells were fixed in methanol for 1 minute at room temperature followed by air drying. The plastic wells of the slides were detached and the slides were washed in 2 changes of 5.0% (v/v) trichloracetic acid, 3 changes of 70% (v/v) ethanol, and 2 changes of absolute ethanol, and then air dried. Next, the slides were stained with 2.0% (w/v) orcein in 50% (v/v) glacial acetic acid for 5 minutes, and destained in absolute ethanol. Then, the slides were immersed in a melted emulsion of Kodak NTB2, air dried in a horizontal position for 1 hour, and exposed for 1 day at room temperature. The exposed emulsion was developed in Dektol (Kodak) for 2 minutes at 16° C., fixed in Kodak Fixer for 5 minutes, and then rinsed in water for 5 minutes. The slides were air dried and mounted under buffered glycerol with coverslips. The slides were examined under a microscopic to ascertain the presence of silver grains over nuclei which resulted from ³H-thymidine which had been phosphorylated and incorporated into DNA by the EHV-1 tk gene encoded on the recombinant plasmids.

Abundant TK-inducing activity was found with both the 15 kb BamHI fragment of pEB15 and the 15 kb HindIII fragment of pEH15 cloned from the 40 kb EHV-1 EcoRI fragment. Since the 15 kb fragment of pEB15 included the BamHI to HindIII region at 5.4 and 15.4 map units on pEH15, but not the 0.0 to 5.4 map units region of pEH15, the location of the EHV-1 tk gene could be specified in the 5.4 to 15.4 kb map units region of pEH15.

E. Fine Mapping of the EHV-1 tk Gene

In order to finely map the EHV-1 tk gene within the 15 kb HindIII fragment subcloned from the 40 kb EHV-1 EcoRI fragment, the following procedures were carried out.

Figure 2:
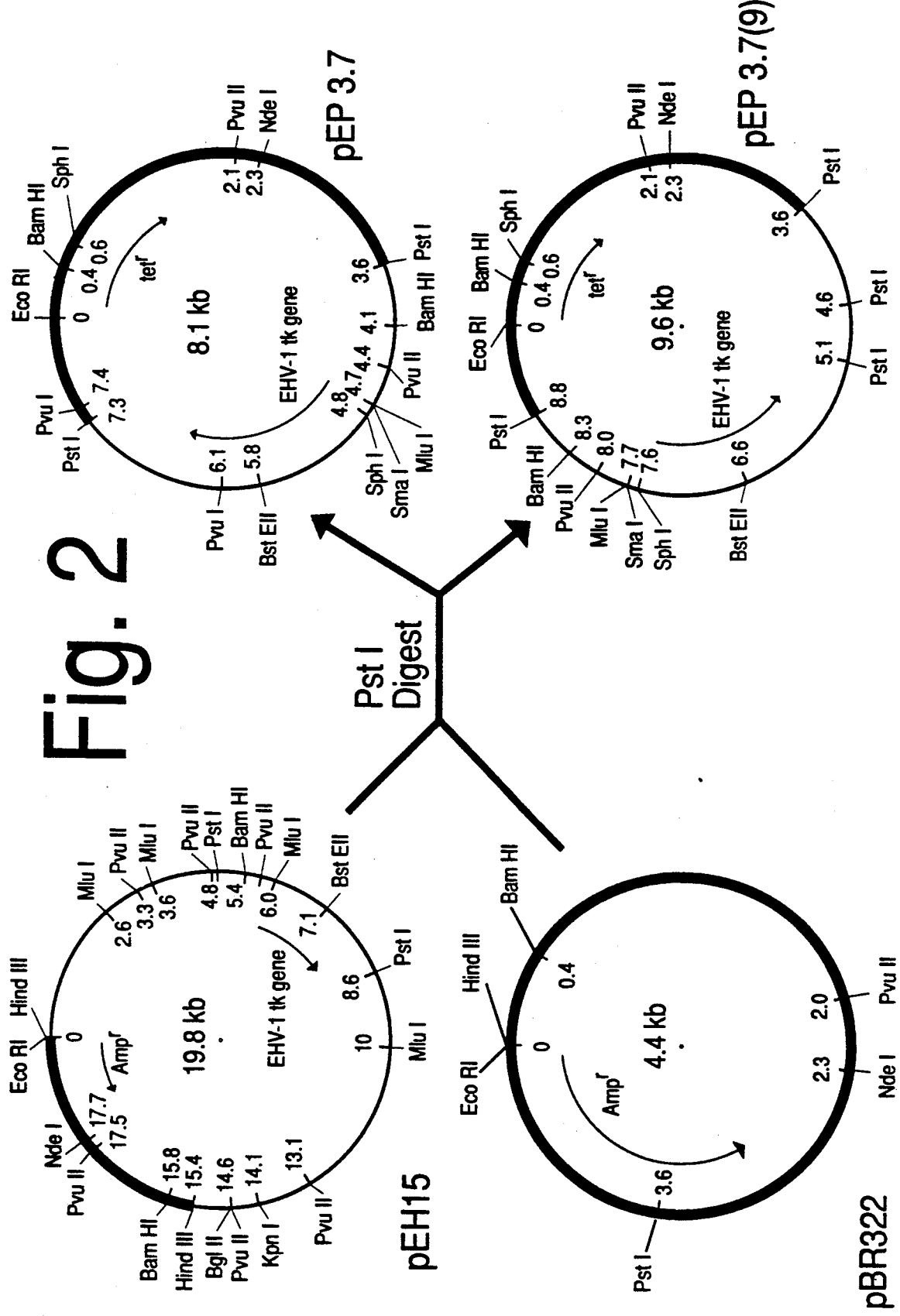
FIG. 2 schematically illustrates, by example, the derivation of subclones pEP 3.7 and pEP 3.7(9) from pEH15, pEP 3.7 and pEP 3.7(9) also contain the EHV-1 tk gene, but in inverse orientations.

PstI fragments of pEH15 were subcloned into the PstI site of pBR322 of DNA (see FIG. 2). More specifically, 2.0 μg of pEH15 were dissolved in 50 μl of a buffer comprising 100 mM NaCl, 10 mM Tris-HCl (pH 7.5), 10 mM MgCl$_2$ and 100 μg/ml of BSA (hereinafter "PstI cutting buffer") and digested with 12 units of PstI (New England Biolabs) for 1 hour at 37° C. Then the reaction was terminated and the DNA collected after ethanol precipitation as described above.

The resulting PstI-digested DNA was mixed with 0.1 μg of PstI-digested, dephosphorylated pBR322, dissolved in 0.05 ml of ligation buffer containing about 1000 units of phage T4 DNA ligase and incubated overnight at 4° C. Then, the reaction was terminated by adding EDTA to 20 mM and heating at 65° C. for 10 minutes. Transformants which were tetracycline resistant were obtained and screened as described in U.S. Pat. No. 4,514,497.

One transformant clone, designated pEP 3.7, contained a 3.7 kb EHV-1 PstI fragment (see FIG. 2). A second transformant clone, designated pEP 3.7(9). contained the same fragment in an inverted orientation and two other small PstI fragments (see FIG. 2). Both of these clones were tested in the transient expression assay described above, and found to contain the EHV-1 tk gene. Next, the restriction nuclease maps for pEP 3.7 and pEP 3.7(9) were determined (see FIG. 2).

To further map the EHV-1 tk gene, five deletions plasmids of pEP 3.7 and pEP 3.7(9) were constructed as follows.

(1) the 1.3 kb PvuI fragment from map position 6.1 to 7.4 of pEP 3.7 was deleted by dissolving 0.25 μg of pEP 3.7 in 50 μl of a buffer comprising 150 mM NaCl, 10 mM Tris-HCl (pH 7.4), 10 mM MgCl$_2$, 10 mM 2-mercaptoethanol, and 100 μg/ml of BSA. (hereinafter "PvuI cutting buffer") and digesting with 4.0 units of PvuI (New England Biolabs) at 37° C. for 1 hour. Then the reaction was terminated by adding CDTA to 20 mM and heating at 65° C. for 30 minutes.

The resulting PvuI-digested pEP 3.7 DNA was ethanol precipitated and collected by centrifugation as described in U.S. Pat. No. 4,514,497, and ligated with 400 units of phage T4 DNA ligase dissolved in 50 μl of ligation buffer for 16 hours at 4° C. Then, the reaction was terminated as described above, and competent *E. coli* K12 RR1 were transformed with the resulting plasmids, and screened for recombinants as described in U.S. Pat. No. 4,514,497.

In this manner, a 6.8 kb plasmid was derived, designated pEP 3.7 dl PvuI, which had the PvuI fragment from map position 6.1 to 7.4 of pEP 3.7 deleted (see FIG. 2).

(2) the 2.3 kb BstEII to EcoRI fragment from map position 5.8 to 8.1 of pEP 3.7 was deleted by dissolving 0.5 μg of pEP 3.7 in 50 μl of EcoRI cutting buffer and digesting with 10 units of EcoRI at 37° C. for 1 hour. Then, the reaction was terminated, and the DNA ethanol precipitated and collected by centrifugation as described above.

The resulting EcoRI-digested pEP 3.7 DNA was dissolved in 50 μl of a buffer comprising 150 mM NaCl 10 mM Tris-HCl (pH 8.0), 10 mM MgCl$_2$ and 100 μg/ml of BSA (hereinafter "BstEII cutting buffer"), and digested with 10 units of BstEII at 60° C. for 1 hour. Then the reaction was terminated by adding CDTA to 20 mM and heating at 65° C. for 30 minutes, and the DNA ethanol precipitated and collected by centrifugation as described above.

The resulting BstEII and EcoRI-digested DNA ends were made flush by dissolving the DNA in 25 μl of a buffer comprising 6.0 mM Tris-HCl (pH 7.5), 6.0 mM MgCl$_2$, 1.0 mM dithiothreitol, and 50 mM NaCl (hereinafter "Hin buffer") and adding 1 unit of Klenow enzyme for 2 minutes at 37° C. and then incubating with 0.1 mM of each of dATP, dCTP, dGTP, dTTP for 2 minutes further at 37° C. Then, the reaction was terminated by heating at 70° C. for 5 minutes and adding an equal volume of 2×ligation buffer. Next, 400 units of phage T4 DNA ligase were added, and the reaction incubated for 16 hours at 4° C. Then, the ligation reaction was terminated as described above, and competent E. coli K12 RR1 were transformed with the resulting plasmids, and screened for recombinants as described above.

In this manner, a 5.8 kb plasmid was derived, designated pEP 3.7 dl BstEII-EcoRI, which had the 2.3 kb BstEII to EcoRI fragment from map position 5.8 to 8.1 of pEP 3.7 deleted (see FIG. 2).

(3) the 0.3 kb BstEII to PvuI fragment from map position 5.8 to 6.1 of pEP 3.7 was deleted by dissolving 1.0 μg of pEP 3.7 in 50 μl of BstEII cutting buffer and digesting with 10 units of BstEII at 60° C. for 1 hour. Then, the reaction was terminated as described above, and the DNA ethanol precipitated and collected by centrifugation as described above.

0.25 μg of the resulting BstEII-digested pEP 3.7 DNA was dissolved in 50 μl of PvuI cutting buffer and partially digested with 0.4 units of PvuI at 37° C. for 1 hour. Then, the reaction was terminated as described above and the DNA ethanol precipitated and collected by centrifugation as described above.

The resulting BstEII and PvuI-digested DNA ends were made flush by dissolving the DNA in 25 μl of Hin buffer and adding 1 unit of Klenow enzyme for 2 minutes at 37° C., and then incubating with 0.1 mM of each of dATP, dCTP, dGTP, dTTP for 2 minutes further at 37° C. Then the reaction was terminated by heating at 70° C. for 5 minutes and adding an equal volume of 2×ligation buffer. Next, 400 units of phage T4 DNA ligase were added, and the reaction incubated for 16 hours at 4° C. Then, the ligation reaction was terminated as described above, and competent E. coli K12 RR1 were transformed with the resulting plasmids, and screened for recombinants as described above.

In this manner, a 7.8 kb plasmid was derived, designated pEP 3.7 dl BstEII-PvuI tiny, which had the 0.3 kb BstEII to PvuI fragment from map position 5.8 to 6.1 of pEP 3.7 deleted (see FIG. 2).

(4) the 1.9 kb SmaI to EcoRI fragment from map position 7.7 to 9.6 of pEP 3.7 (9) was deleted by dissolving 0.5 μg of pEP 3.7 (9) in 50 μl of EcoRI cutting buffer and digesting with 10 units of EcoRI at 37° C. for 1 hour. Then, the reaction was terminated as described above, and the DNA ethanol precipitated and collected by centrifugation as described above.

0.5 μg of the resulting EcoRI-digested pEP 3.7 (9) DNA was dissolved in 50 μl of a buffer comprising 20 mM KCl, 6.0 mM Tris-HCl (pH 8.0), 6.0 mM MgCl$_2$, 6.0 mM 2-mercaptoethanol, and 100 μg/ml of BSA, (hereinafter "SmaI cutting buffer") and digested with 5 units of SmaI at 25° C. for 1 hour. Then, the reaction was terminated and the DNA ethanol precipitated and collected by centrifugation as described above.

The resulting EcoRI and SmaI-digested DNA ends were made flush by dissolving the DNA in 25 μl of Hin buffer containing 0.1 mM of each of dATP, dCTP, dGTP, dTTP, adding 2 units of Klenow enzyme, and incubating for 30 minutes at 25° C. Then, the reaction was terminated by heating at 70° C. for 5 minutes and adding an equal volume of 2×ligation buffer. Next, 400 units of phage T4 DNA ligase were added, and the reaction incubated for 16 hours at 4° C. Then, the ligation reaction was terminated as described above, and competent E. coli K12 RR1 were transformed with the resulting plasmids and screened for recombinants as described above.

In this manner, a 7.7 kb plasmid was derived, designated pEP 3.7 (9) dl SmaI-EcoRI, which had a 1.9 kb fragment from map position 7.7 to 9.6 of pEP 3.7 (9) deleted (see FIG. 2).

(5) the 3.0 kb BstEII-EcoRI fragment from map position 6.6 to 9.6 of pEP 3.7 (9) was deleted by dissolving 0.5 μg of pEP 3.7 (9) in 50 μl of EcoRI cutting buffer and digesting with 10 units of EcoRI at 37° C. for 1 hour. Then the reaction was terminated as described above, and the DNA ethanol precipitated and collected by centrifugation as described above.

The resulting EcoRI-digested pEP 3.7 (9) DNA was dissolved in 50 μl of BstEII cutting buffer and digested with 10 units of BstEII at 60° C. for 1 hour. Then, the reaction was terminated as described above, and the DNA ethanol precipitated and collected by centrifugation as described above.

The resulting BstEII and EcoRI-digested DNA ends were made flush by dissolving the DNA in 25 μl of Hin buffer and adding 1 unit of Klenow enzyme for 2 minutes at 37° C. and then incubating with 0.1 mM of each of dATP, dCTP, dGTP, dTTP for 2 minutes further at 37° C. Then, the reaction was terminated by heating at 70° C. for 5 minutes and adding an equal volume of 2×ligation buffer. Next, 400 units of phage T4 DNA ligase were added, and the reaction incubated for 16 hours at 4° C. Then, the ligation reaction was terminated as described above, and competent E. coli K12 RR1 were transformed with the resulting plasmids, and screened for recombinants as described above.

In this manner, a 6.6 kb plasmid was derived, designated pEP 3.7 (9) dl BstEII-EcoRI, which had the 3.0 kb BstEII to EcoRI fragment from map position 6.6 to 9.6 of pEP 3.7 (9) deleted (see FIG. 2).

As discussed above, the deletion plasmids of pEP 3.7 and pEP 3.7 (9) were obtained so as to define the fragments containing a functional, intact, EHV-1 tk gene more precisely. The results obtained when the above plasmids were tested for the ability to induce TK activity in the transient expression assay described above are shown in Table 1 below.

TABLE 1

| recombinant plasmid | map position of deletion | TK-inducing activity |
|---|---|---|
| pEP 3.7 dl PvuI | 6.1 to 7.4 | no |
| pEP 3.7 dl BstEII-EcoRI | 5.8 to 8.1 | no |
| pEP 3.7 dl BstEII-PvuI tiny | 5.8 to 6.1 | no |
| pEP 3.7(9) dl SmaI-EcoRI | 7.7 to 9.6 | yes |
| pEP 3.7(9) dl BstEII-EcoRI | 6.6 to 9.6 | no |

The results shown in Table 1 above demonstrate that the EHV-1 tk gene is present in a 2.6 kb SmaI to PstI fragment at map position 4.7 to 7.3 of pEP 3.7 because deletion of the sequences on the other side of the SmaI site does not result in loss of TK activity. To more precisely characterize the EHV-1 tk gene, this region was sequenced as follows.

The EHV-1 tk gene was sequenced by the Sanger dideoxynucleotide chain termination method (Sanger, F. et al, Proc. Natl. Acad. Sci., USA, 74:5463-5467 (1977); and U.S. Pat. No. 4,514,497) from single stranded M13 DNA containing EHV-1 inserted fragments as follows.

Three M13 clones were constructed from DNA fragments derived from pEP 3.7. XmaI is an isoschizomer of SmaI which produces cohesive ends that are easier to clone than the blunt ends produced by SmaI. Hence, as described in more detail below, the sense strand of the EHV-1 tk gene was sequenced by cloning the SmaI (XmaI) to PstI fragment from pEP 3.7 at map position 4.7 to 7.3 (see FIG. 2) into the XmaI to PstI site of M13mp19. Next, a nested set of unidirectional deletion mutants were constructed using ExonucleaseIII digestion (Henikoff, S., Gene, 28:351-359 (1984)). Gaps in the sequence were filled in by utilizing synthetic oligonucleotide primers.

As discussed in more detail below, synthetic oligonucleotides based upon the sense strand sequence were used to sequence the reverse complement strand from two constructs by cloning the (1) PstI to BstEII fragment from pEP 3.7 at map position 7.3 to 5.8 into the PstI to SmaI sites of M13mp18, and (2) BstEII to PstI fragment from pEP 3.7 at map position 5.8 to 3.6 into the SmaI to PstI sites of M13mp19.

1. Sense Strand sequencing 2.0 μg of pEP 3.7 and 1.0 μg of M13mp19 RF DNA (Bethesda Research Laboratories) were dissolved in 10 μl of a buffer comprising 25 mM NaCl, 10 mM Tris-HCl (pH 7.5), 10 mM $MgCl_2$, 10 mM 2-mercaptoethanol, and 100 μg/ml of BSA (hereinafter "XmaI cutting buffer") and digested with 5 units of XmaI at 37° C. for 2 hours. Next, the volume was increased to 50 μl by adding 2.0 μl of PstI (40 units), 5.0 μl of 10×PstI cutting buffer and 33 l of water, followed by digestion at 37° C. for one hour. Then, the reaction was terminated with 90% (v/v) phenol, and the DNA ethanol precipitated and collected by centrifugation as described above.

The resulting XmaI and PstI-digested pEP 3.7 DNA was suspended in 20 μl of ligation buffer and ligated with 400 units of phage T4 DNA ligase at 4° C. for 16 hours. The volume was then increased to 160 μl with TE buffer and the reaction terminated by heating at 65° C. for 10 minutes. Competent E. coli JM103 were transformed with the resulting DNA and recombinant phage screened, and single stranded DNA prepared for sequencing as described in U.S. Pat. No. 4,514,497.

In this manner, a recombinant clone was obtained with the XmaI to PstI fragment at map position 4.7 to 7.3 of pEP 3.7 inserted into the XmaI to PstI site of M13mp19. This clone was designated M13mp19/XmaI-PstI.

Next, a nested set of unidirectional deletion mutants was prepared by dissolving 5.5 μg of M13mp19/XmaI-PstI in 100 μl of a buffer comprising 10 mM Tris-HCl (pH 7.4), 10 mM $MgCl_2$, 10 mM 2-mercaptoethanol, and 100 μg/ml of BSA (hereinafter "SacI cutting buffer") and digesting with 20 units of SacI (New England Biolabs) at 37° C. for 2 hours. Then, the reaction was terminated by adding CDTA to 20 mM and heating at 65° C. for 30 minutes.

The resulting SacI-digested M13mp19/XmaI-PstI DNA was ethanol precipitated and collected by centrifugation in 100 μl of XmaI cutting buffer and digested with 20 units of XmaI at 37° C. for 3 hours. Then, the reaction was terminated and the DNA ethanol precipitated and collected by centrifugation as described above.

The resulting XmaI and SacI-digested M13mp19/XmaI-PstI DNA was resuspended in 55 μl of a buffer comprising 66 mM Tris-HCl (pH 8.0), and 0.6 mM $MgCl_2$, and digested with 360 units of ExonucleaseIII (Bethesda Research Laboratories) at 37° C., 5.0 μl aliquots were removed at 30 second intervals, and mixed with 15 μl of a buffer comprising 0.2M NaCl, and 5.0 mM EDTA (pH 8.0), and the reaction terminated by heating at 70° C. for 10 minutes. The DNA was then ethanol precipitated and collected by centrifugation.

The resulting ExonucleaseIII-digested DNA was dissolved in 20 μl of a buffer comprising 30 mM sodium acetate (pH 4.6), 50 mM NaCl, and 1.0 mM $ZnCl_2$ (hereinafter "mung bean nuclease buffer"). and the ends made flush by digestion with 150 units of mung bean nuclease (Pharmacia) at 37° C. for 15 minutes. Then, the reaction was terminated by adding 2.0 μl of 4.0% (w/v) SDS, 2.0 μl of 0.5 M Tris-HCl (pH 9.5), 15 μl of 90% (v/v) phenol, and 15 μl of chloroform, vortexing, and separating the aqueous phase from the organic phase by centrifugation. The aqueous phase was extracted with ether, and the DNA was ethanol precipitated and collected by centrifugation.

The resulting DNA was resuspended in 20 μl of ligation buffer and ligated with 400 units of phage T4 DNA ligase at 4° C. for 16 hours. The volume was then increased to 160 μl with TE buffer and the reaction terminated by heating at 65° C. for 10 minutes. Competent E. coli JM103 were transformed with the resulting DNA and recombinant phage screened, and single stranded DNA prepared for sequencing as described in U.S. Pat. No. 4,514,497.

2. Complementary Strand Sequencing

The PstI to BstEII fragment from pEP 3.7 at map position 7.3 to 5.8 was transferred into the PstI to SmaI site of M13mp18 as follows.

4.0 μg of pEP 3.7 was dissolved in 100 μl of BstEII cutting buffer and digested with 20 units of BstEII at 60° C. for 2 hours. Then, the reaction was terminated with phenol, and the DNA in the aqueous phase was ethanol precipitated and collected by centrifugation as described above.

The resulting BstEII-digested pEP 3.7 DNA was resuspended in 100 μl of mung bean nuclease buffer and digested with 2 units of mung bean nuclease at 37° C. for 15 minutes. Then, 4.0 μl of 10% (w/v) SDS, 10 μl of 0.5M Tris-HCl (pH 9.5), and 10 μl of 8.0M LiCl were added. The mixture was extracted with an equal volume of 90% (v/v) phenol:chloroform (1:1), ether extracted, and the DNA was ethanol precipitated.

The resulting DNA was resuspended in 20 μl of PstI cutting buffer and digested with PstI at 37° C. for 2 hours. Then, the reaction was terminated with phenol, and the DNA ethanol precipitated and collected by centrifugation as described above.

Next, the recipient cloning vector. i.e., 1.0 μg of M13 mp18 RF DNA, was dissolved in 50 μl of SmaI cutting buffer and digested with 5 units of SmaI at 37° C. for 2 hours. Then, the reaction was terminated with phenol, and the DNA ethanol precipitated and collected by centrifugation as described above.

The resulting SmaI-digested M13mp18 RF DNA was resuspended in 10 μl of PstI cutting buffer, and digested with an excess of PstI at 37° C. for 2 hours. Then, the reaction was terminated with phenol, and the DNA ethanol precipitated and collected by centrifugation as described above.

The resulting PstI and SmaI-digested M13mp18 RF DNA and BstEII and PstI-digested pEP 3.7 DNA were resuspended in 20 μl of ligation buffer and ligated with 400 units of phage T4 DNA ligase at 4° C. for 16 hours. The volume was then increased to 160 μl with TE buffer and the reaction terminated by heating at 65° C. for 10 minutes. Competent $E.$ $coli$ JM103 were transformed with the resulting DNA and recombinant phage screened, and single stranded DNA for sequencing prepared as described above.

The BstEII to PstI fragment of pEP 3.7 for map position 5.8 to 3.6 was also cloned into the SmaI to PstI site of M13mp18 as described above. An EcoRI to PstI fragment of this M13mp18 recombinant was transferred to the PstI to EcoRI site of M13mp19 as follows.

2.0 μg of M13mp19 or M13mp18/BstEII-PstI (5.8 to 3.6 map position) was digested with PstI and EcoRI as described above. The resulting DNA was separated by electrophoresis on an agarose gel and the EcoRI to PstI fragment comprising a 2.2 kb fragment containing the EHV-1 BstEII to PstI sequence was extracted from an excised slice after ethidium bromide staining and UV transillumination, and then purified by phenol extraction. The EcoRI and PstI-digested M13mp19 was extracted and purified in the same manner.

The resulting EcoRI and PstI-digested M13mp19 DNA and 2.2 kb fragment from M13mp18/BstEII-PstI was resuspended in 20 μl of ligation buffer and ligated with 400 units of phage T4 DNA ligase at 4° C. for 16 hours. The volume was then increased to 160 μl with TE buffer and the reaction terminated by heating at 65° C. for 10 minutes. Competent $E.$ $coli$ JM103 were transformed with the resulting DNA, and recombinant phage screened, and single stranded DNA was prepared for sequencing as described above.

Upon sequencing the resulting DNA, the sequence of the EHV-1 tk gene shown in FIG. 3 was obtained.

G. Construction of pSV2β-gal(BglII-BglII)

In order to obtain a tk− insertion mutant of EHV-1 which expressed a foreign protein, a plasmid was first constructed containing the β-Galactosidase gene inserted into a DNA fragment containing a promoter, polyadenylation and splicing sequences as follows.

Plasmid pSV2gpt, which contains the *E. coli* gpt gene adjacent to the SV40 early promoter and SV40 splice, termination and polyadenylation sequences, was obtained from the American Type Culture Collection (ATCC No. 37145) (see FIGS. 4 and 5) (Berg. P. et al. *Mol. Cell. Biol.*, 1(5):449–459 (1981)). At the restriction sites between the cloning vector and the SV40 insert of this plasmid, BglII restriction nuclease recognition sites were introduced by the following procedures.

First, an internal BglII site at map position 2.5 of pSVgpt was eliminated by deleting a HindIII to BglII fragment at map position 2.5 to 2.6 and replacing such with a synthetic adaptor bridge as follows (see FIG. 4).

1.0 μg of pSV2gpt was dissolved in 100 μl of HindIII cutting buffer and digested with 20 units of HindIII for 2 hours at 37° C. Then, the reaction was terminated by adding CDTA to 20 mM, and heating at 65° C. for 30 minutes. Next, a ½ volume of 7.5M ammonium acetate was mixed with the reaction, and the DNA was ethanol precipitated and collected by centrifugation as described above.

The resulting HindIII-digested DNA was dissolved in 100 μl of a buffer comprising 100 mM NaCl 10 mM Tris-HCl (pH 7.4), 10 mM $MgCl_2$, 10 mM 2-mercaptoethanol, and 100 μg/ml of BSA (hereinafter "BglII cutting buffer") and digested with 12 units of BglII enzyme for 2 hours at 37° C. Then, the reaction was terminated by digestion with 100 μg/ml Proteinase K for 1 hour, at 37° C., and vortexing with an equal volume of 90% (v/v) phenol. The resulting DNA in the aqueous phase was extracted with ether dialyzed against 0.1×TE buffer and ethanol precipitated as described above.

The bridging adaptor oligonucleotides were synthesized by the Phosporamidite method on an automated DNA synthesizer (Systec, Inc.), according to the manufacturer's instructions, then cleaved from the CPG-support in concentrated ammonium hydroxide for 1 hour at room temperature. The resulting supernatant was heated to 55° C. for 12 hours to deblock the bases, and lyopholized and desalted on P-4 gels (Bio-Rad, Inc.). The oligonucleotides were purified on 16% (w/v) polyacrylamide gels, extracted in 1.0M triethylamine bicarbonate and desalted on Sea-Pak cartridges (Lo, K. M. et al. *Proc. Natl. Acad. Sci.*, USA, 81:2285–2289 (1984)). The adaptor had the following sequence:

```
5'-AGCTTACGCGTCTC
       ATGCGCAGAGCTAG-3'
```

This adaptor has a HindIII cohesive end regenerated upon ligation to a HindIII terminus and a BglII cohesive end which is not regenerated upon ligation to a BglII terminus.

1.0 μg of each oligonucleotide was annealed in 10 μl of 0.1×TE buffer at 70° C. for 5 minutes followed by slow cooling to 4° C. The annealed oligonucleotides were added to the HindIII and, BglII-digested pSV2gpt dissolved in 50 μl of ligation buffer, and ligated with 1000 units of phage T4 DNA ligase at 4° C. overnight. Then, the reaction was terminated with 3.0 μl of 0.25M EDTA, and heated at 70° C. for 10 minutes to dissociate the oligonucleotides which had not been covalently bound to the vector through the vector donor 5'-phosphate. The mixture was then chilled on ice to permit recircularization of the plasmid by annealing of the complementary single stranded oligonucleotides covalently bound to each terminus. Competent *E. coli* K12 RR1 were transformed with the resulting plasmids, and colonies screened as described above.

In this manner, a recombinant plasmid was derived and designated pSV2gpt(dl H-Bgl). This plasmid differed from the parental plasmid by the elimination of the BglII site at map position 2.5 (see FIG. 4). and deletion of a a 0.1 kb fragment from map positions 2.5 to 2.6 of pSV2gpt.

A BglII site was then introduced at the EcoRI site at map position 0 of pSV2gpt(dl H-Bgl) as follows.

2.0 μg of pSV2gpt(dl H-Bgl) was dissolved in 50 μl of EcoRI cutting buffer, and digested with 20 units of EcoRI for 2 hours at 37° C. Then, the reaction was terminated by digestion with Proteinase K, and extracted with phenol as described above. The aqueous phase obtained after phase separation by centrifugation was ether extracted and dialyzed against 0.1×TE buffer. The resulting DNA containing solution was mixed with a 1/10th volume of 3.0M sodium acetate, and 2 volumes of ethanol. After an overnight incubation at −20° C. the resulting DNA was ethanol precipitated, collected by centrifugation as described above and air dried.

Next, an adaptor having the following sequence, was synthesized and purified as described above:

```
5'-AATTCGATATCAGATCT
       GCTATAGTCTAGATTAA-3'
```

This adaptor has EcoRI cohesive ends and an internal BglII site. The oligonucleotides were annealed and ligated to the EcoRI-digested pSV2gpt(dl H-Bgl). as described above. Then, the reaction was terminated and the plasmid recircularized as described above. Competent *E. coli* K12 RR1 were transformed with the resulting plasmids, and colonies screened as described above.

In this manner, a recombinant plasmid was derived and designated pSV2gpt(dl H-Bgl):EcoRI adaptor. This plasmid differed from the parental plasmid by the introduction of an BglII site at map position 0 (see FIG. 4).

A BglII site was then introduced at the PvuII site at map position 2.8 of pSV2gpt(dl H-Bgl):EcoRI adaptor as follows.

2.0 μg of pSV2gpt(dl H-Bgl):EcoRI adaptor was dissolved in 100 μl of a buffer comprising 60 mM NaCl, 10 mM Tris-HCl (pH 7.5). 10 mM MgCl$_2$, 6.0 mM 2-mercaptoethanol, and 100 μg/ml of BSA (hereinafter "PvuII cutting buffer") and digested with 20 units of PvuII (New England Biolabs) for 1 hour at 37° C. Then, the reaction was terminated with Proteinase K and extracted with phenol as described above. The resulting DNA was dialyzed and ethanol precipitated and collected by centrifugation as described above.

Next an adaptor having the following sequence, was synthesized and purified as described above:

```
5'-GAGCTCAGATCTGTCGAC
     CTCGAGTCTAGACAGCTG-3'
```

This adaptor possesses blunt ends compatible with PvuII termini and an internal BglII site. The oligonucleotides were annealed and ligated to the PvuII-digested pSV2gpt(dl H-Bgl):EcoRI adaptor, as described above. Then, the reaction was terminated and the plasmid recircularized as described above. Competent *E. coli* K12 RR1 were transformed with the resulting plasmids, and colonies screened as described above.

In this manner, a recombinant plasmid was derived and designated pSV2gpt(dl H-Bgl):BglII-BglII. This plasmid differed from the parental plasmid by the introduction of a BglII site at map position 2.8 (see FIG. 4).

Thereafter, the gpt gene within pSV2gpt(dl H-Bgl):BglII-BglII was then replaced with the β-Gal gene as follows.

Figure 5:
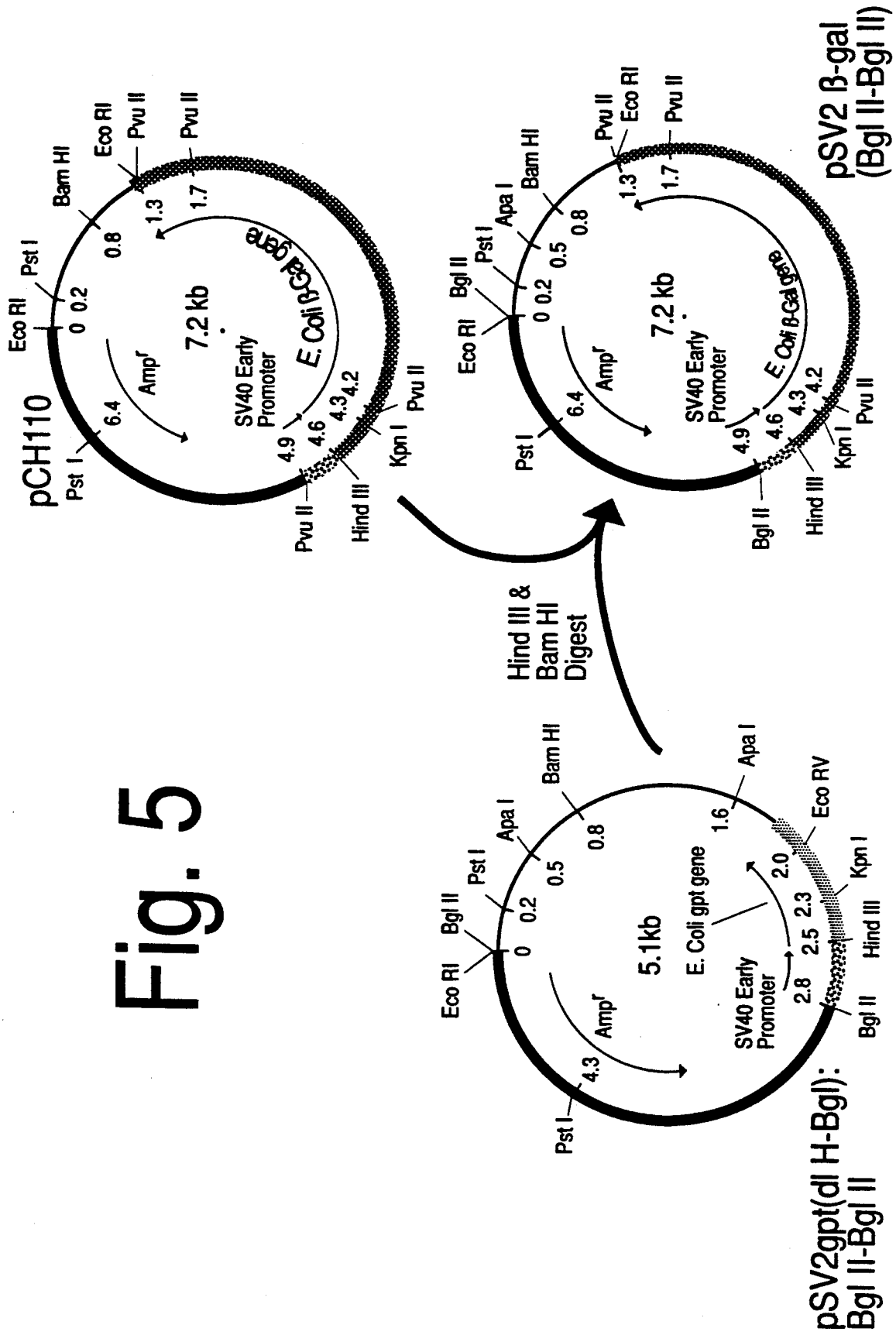
FIG. 5 schematically illustrates, by example, the derivation of pSV2β-gal(BglII-BglII). This plasmid contains the SV40 early promoter adjacent to the E. coli β-galactosidase gene.

2.0 μg of pSV2gpt(dl H-Bgl):BglII-BglII and 2.0 μg of pCH110 (Pharmacia), which contains the β-Gal gene (see FIG. 5), were dissolved in 100 μl of HindIII cutting buffer and digested with 40 units of HindIII for 6 hours at 37° C. Then, the reaction was terminated by adding CDTA to 20 mM, and ammonium acetate was added to 2.5M. Next the DNA was precipitated with 2 volumes of ethanol and collected by centrifugation as described above.

The resulting HindIII-digested pSV2gpt(dl H-Bgl):BglII-BglII and HindIII-digested pCH110 were dissolved in 100 μl of BamHI cutting buffer and digested with 75 units of BamHI for 6 hours at 37° C. Then, the reaction was terminated by digestion with Proteinase K and extracted with phenol as described above. Next the DNA was dialyzed and ethanol precipitated, and collected by centrifugation as described above.

The resulting HindIII and BamHI-digested pCH110 and HindIII and BamHI-digested pSV2gpt(dl H-Bgl):BglII-BglII were dissolved in 50 μl of ligation buffer and ligated with 1000 units of phage T4 DNA ligase for 16 hours at 4° C. Then, the reaction was terminated by adding EDTA to 20 mM and heating at 65° C. for 10 minutes. Competent *E. coli* K12 RR1 were transformed with the resulting plasmids, and colonies screened as described above.

In this manner, a recombinant plasmid was derived and designated pSV2β-gal(BglII-BglII). This plasmid has the β-Gal gene under the control of the SV40 early promoter and polyadenylation and splice signals, and can be mobilized for transfer to another plasmid by excision with BglII (see FIG. 5).

H. Construction of pEP3.7/SV2β-gal

Figure 6:
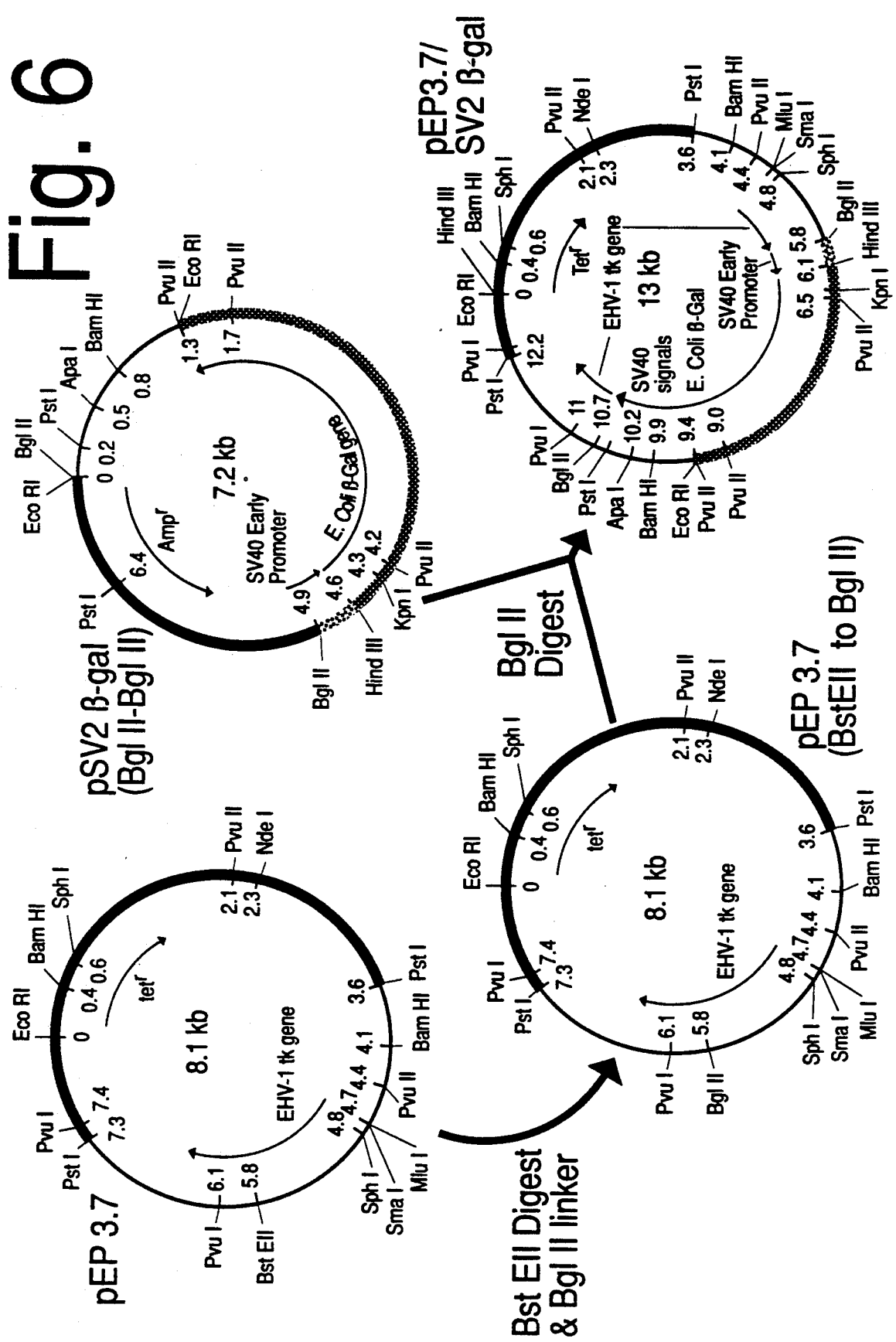
FIG. 6 schematically illustrates, by example, the derivation of pEP 3.7/SV2β-gal. This plasmid contains a DNA fragment, containing the SV40 early promoter adjacent to the E. coli β-galactosidase gene, which has been inserted into the BglII restriction nuclease site of the EHV-1 tk gene.

First, the BstEII site at position 5.8 of pEP 3.7 was converted to a BglII site by the addition of a BglII linker as follows (see FIG. 6).

1.0 μg of pEP 3.7 was dissolved in 50 μl of BstEII cutting buffer and digested with 5 units of BstEII for 2 hours at 60° C. Then, the reaction was terminated by adding CDTA to 20 mM and the resulting DNA precipitated by adding ammonium acetate to 2.5M and adding 2 volumes of ethanol. After an overnight incubation at −20° C. the DNA was collected by centrifugation and air dried as described above.

The resulting BstEII-digested pEP 3.7 was dissolved in 25 μl of Hin buffer containing 0.1 mM of each of dATP, dCTP, dTTP, dGTP and 1 unit of Klenow enzyme, and incubated at room temperature for 30 minutes to fill in the recessed 3'-ends of the BstEII-digested termini. Then, the reaction was terminated by heating at 70° C. for 5 minutes, and ethanol precipitated and collected by centrifugation as described above.

Next, 1.0 μg of an 8-mer BglII linker (New England Biolabs) was phosphorylated in 10 μl of ligation buffer with 10 units of polynucleotide kinase (New England Biolabs) for 1 hour at 37° C.

The BstEII-digested pEP 3.7 filled in with Klenow enzyme was then dissolved in 10 μl of ligation buffer and was combined with the phosphorylated BglII linker, and ligated with 400 units of phage T4 DNA ligase for 5 hours at 22° C. and 16 hours at 4° C.

The resulting BstEII-digested pEP 3.7 with polylinkers attached to the BstEII termini was separated from unattached linkers by centrifugation through a SE-LECT-6L column (5 Prime-3 Prime Inc.), a spin filter containing a gel filtration media, according to the manufacturer's instructions. Next, the polylinkers attached to the BstEII termini of BstEII-digested pEP 3.7 were digested with 5 units of BglII for 2 hours at 37° C. in 50 μl of BglII cutting buffer. Then, the reaction was terminated by adding CDTA to 20 mM and heating at 65° C. for 10 minutes. Next, the DNA was ethanol precipitated and collected by centrifugation as described above.

The resulting DNA was dissolved in 50 μl of ligation buffer containing 400 units of phage T4 DNA ligase and incubated at 4° C. for 16 hours. Then, the reaction was terminated by adding EDTA to 20 mM and heating at 65° C. for 10 minutes. Competent *E. coli* K12 RR1 were transformed with the resulting plasmids, and tetracycline resistant colonies screened as described above.

In this manner, a recombinant plasmid was derived and designated pEP 3.7(BstEII to BglII). This plasmid has the BstEII site at position 5.8 of pEP 3.7 eliminated and replaced with a BglII site (see FIG. 6).

Next, the 4.9 kb fragment from pSV2β-gal(BglII-BglII). containing the β-Gal gene under the control of SV40 expression signals, was excised with BglII and inserted into the EHV-1 tk gene at the new BglII site (map positions 5.8) of pEP 3.7(BstEII to BglII) as follows (see FIG. 6).

2.0 μg of pSV2β-gal(BglII-BglII) and 2.0 μg of pEP 3.7(BstEII to BglII) were dissolved in 100 μl of BglII cutting buffer and digested with 16 units of BglII for 2 hours at 37° C. Then, the reaction was terminated with Proteinase K and phenol extracted, and the DNA dialyzed, ethanol precipitated and collected by centrifugation as described above.

The resulting BglII-digested pSV2β-gal(BglII-BglII) and BglII-digested pEP 3.7(BstEII to BglII) were dissolved in 50 μl of ligation buffer containing 400 units of phage T4 DNA ligase and incubated at 4° C. for 16 hours. Then, the reaction was terminated by adding EDTA to 20 mM and heating at 65° C. for 10 minutes. Competent *E. coli* K12 RR1 were transformed with the resulting plasmids, and tetracycline resistant colonies screened as described above.

In this manner, a recombinant plasmid was derived and designated pEP 3.7/SV2β-gal. This plasmid has the 4.9 kb BglII fragment from pSV2β-gal(BglII-BglII) inserted into the BglII site of pEP 3.7(BstEII to BglII) (see FIG. 6).

I. Construction of a tk⁻EHV-1 Insertion Mutant Expressing the β-Gal Gene From an Insertion in the EHV-1 tk Gene The particular strain chosen for the recombination was EHV-1 strain Rhinoquin TM. However as discussed above, other tk+EHV-1 strains could equally be employed without departing from the spirit and scope of the present invention.

In order to obtain, by homologous recombination, a tk⁻EHV-1 insertion mutant, it was necessary to start with the intact DNA of EHV-1 strain Rhinoquin TM and a hybrid plasmid containing an insertion in the coding region of the EHV-1 tk gene. The progeny virus obtained following this type of cross mainly comprise parental tk+EHV-1 strain Rhinoquin TM.

However, the tk⁻insertion recombinant virus could be identified by the gain of the β-Gal gene, which produced blue virus plaques distinct from the clear plaques of the parental tk+EHV-1 strain Rhinoquin TM.

The hybrid plasmid chosen for the recombination was pEP 3.7/SV2β-gal. However, as discussed above, other hybrid plasmids containing EHV-1 functional promoters or foreign genes of other infectious agents of disease, alone or along with a deletion in the EHV-1 tk gene, could equally be employed to obtain other tk⁻EHV-1 insertion mutants without departing from the spirit and scope of the present invention.

The construction of a recombinant tk insertion mutant of EHV-1 expressing the β-Gal gene was carried out as follows.

RAB-9 cells were seeded in 60 mm Petri dishes ($0.2 \times 10^6$ cells per dish) and incubated at 37° C. for 48 hours. Then, the following sterile solutions were added to a test tube in sequential order:

(1) 0.02 ml of a 50 μg/ml solution of tk+EHV-1 strain Rhinoquin TM DNA in TE buffer;

(2) 0.2 ml of a 10 μg/ml solution of hybrid plasmid pEP 3.7/SV2β-gal;

(3) 0.65 ml of water;

(4) 1.0 ml of a 20 μg/ml solution of salmon sperm DNA in 2×Herpes buffer solution comprising 16 g/l NaCl, 0.74 g/l KCl, 0.25 g/l $Na_2HPO_4.2H_2O$, 2.0 g/l glucose, 10 g/l Herpes (pH 7.05) (hereinafter "2×Herpes buffer solution"); and (5) 0.13 ml of 2.0M $CaCl_2$.

The resulting solution was mixed by inversion and kept at room temperature for 30 minutes while a DNA-calcium phosphate precipitate formed. Then, 0.5 ml of the suspension containing the DNA-calcium phosphate precipitate was added directly to 5.0 ml of growth medium and plated on RAB-9 cells which had been seeded in 60 mm Petri dishes 48 hours earlier. The cells were incubated at 37° C. for 4 hours. Then, the media was aspirated, and the monolayer rinsed with 5.0 ml of fresh growth media, followed by the addition of 1.0 ml of a solution comprising 1×Herpes buffer solution plus 20% (w/v) glucose plus 10% (v/v) Dimethylsulfoxide (DMSO). After a 5 minute incubation at room temperature, the solution, was aspirated, and the monolayer rinsed with media again. Then, 5.0 ml of fresh growth media containing $0.5 \times 10^6$ Vero cells, which had been prepared as a cell suspension immediately prior, was added to the transfected RAB-9 cells. The culture was incubated at 37° C. for 4 days until extensive cytopathic effects occurred. Virus harvests were made as described above and stored at −80° C.

The virus harvests were then titrated in Vero cells under an agar overlay as described in U.S. Pat. No. 4,514,497 with the modification, that the second agar overlay had the neutral red indicator dye replaced with 0.1 mg/ml of MTT (Sigma Chemical) and 330 μg/ml of X-Gal (Boehringer-Mannheim). Virus plaques of the parental tk+virus, i.e., EHV-1 strain Rhinoquin TM were clear against a pale purple background, whereas several blue plaques were at lower dilutions. The blue plaques were "picked" by inserting a capillary pipette into the agar over the plaque and aspirating and dispensing the material into 1.0 ml of growth medium. The "picked" plaques contained virus in an amount of from about $10^4$ to $10^5$ p.f.u./ml and were stored at −80° C.

Working stocks of virus from several of the "picked" blue plaques were prepared by infecting monolayer cultures of about $10^7$ Vero cells with 1.0 ml of virus from each plaque picked and incubating at 37° C. for 2-3 days until extensive cytopathic effects were observed. A blue plaque was subjected to several cycles of plaque purification, and then analyzed further.

In this manner, virus clone EHV-1 (β-Gal) was obtained. EHV-1 (β-Gal) has been deposited with at the American Type Culture Collection under ATCC No. VR-2238. EHV-1 (β-Gal) was also plaqued in fetal equine brain cells and shown to produce blue plaques under the same conditions, demonstrating for the first time that the SV40 promoter was active in equine cells.

X-Gal is a colorless compound which is a substrate for the β-Galactosidase encoded by the β-galactosidase gene. The enzymatic action of β-Galactosidase upon X-Gal converts the colorless substrate into a blue colored compound. This reaction is accelerated by the presence of MTT. The conversion of X-Gal into a blue precipitate at the locations of virus plaques demonstrates that the recombinant virus EHV-1 (β-Gal) expresses a foreign protein (*E. coli* β-Galactosidase).

EXAMPLE 2

Production of tk⁻ Deletion Mutants of EHV-1

A. Construction of pEP 3.7/IBI30

Figure 7:
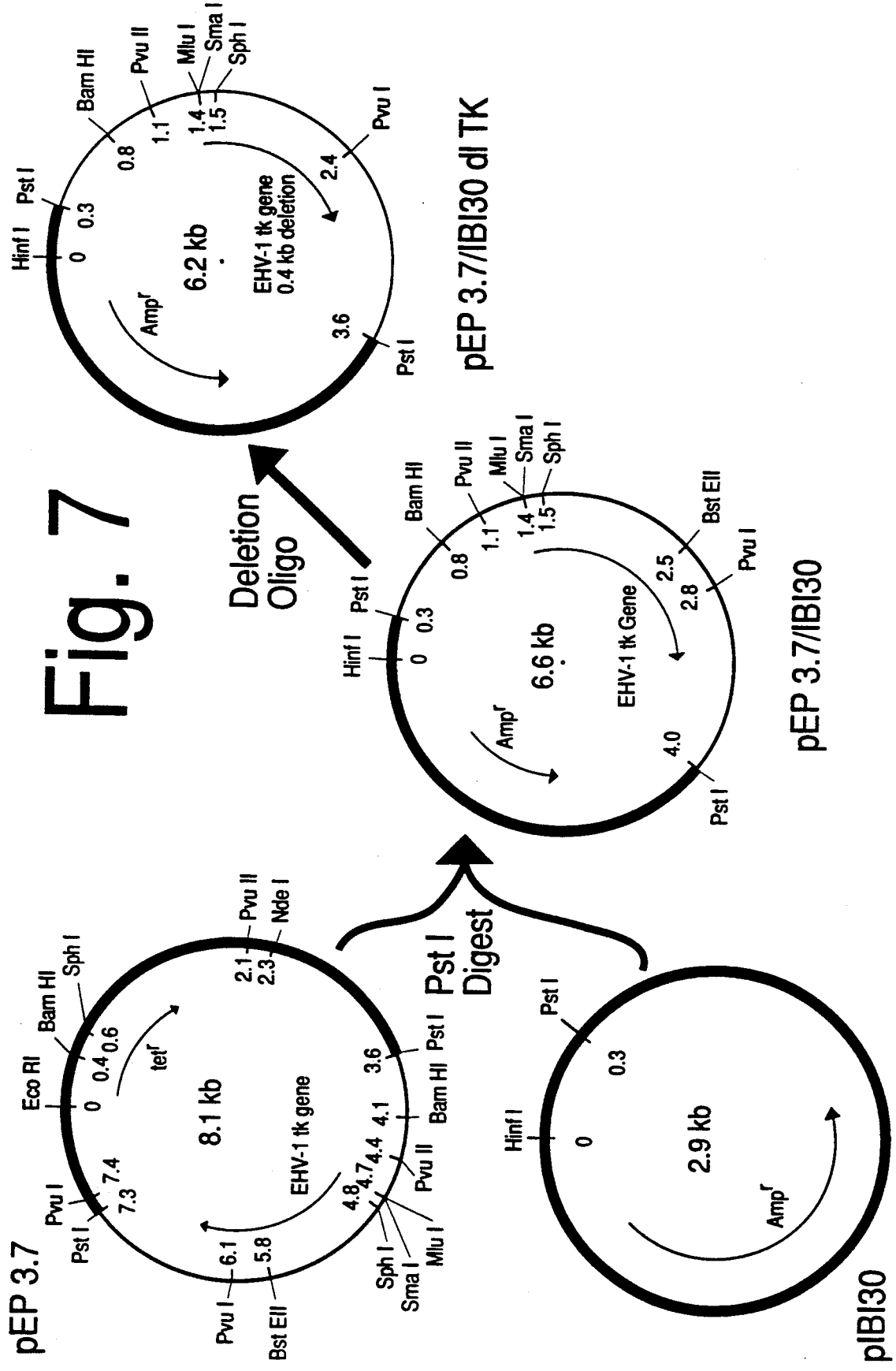
FIG. 7 schematically illustrates, by example, the derivation of pEP 3.7/IBI30 dl TK. This plasmid is obtained from pEP 3.7 (see FIG. 2) and contains a 0.4 kb deletion in the EHV-1 tk gene.

The 3.7 kb PstI fragment from pEP 3.7 containing the EHV-1 tk gene was transferred to the cloning vector pIBI30 (International Biotechnologies, Inc.). pIBI30 contains an origin for fd phage and can be used to generate single stranded DNA for deletion mutagenisis (see FIG. 7).

2.0 µg of pEP 3.7 and 2.0 µg of pIBI30 were dissolved in 100 µl of PstI cutting buffer and digested with 20 units of PstI for 1 hour at 37° C. Then, the reaction was terminated with Proteinase K and extracted with phenol, and the DNA was dialyzed and ethanol precipitated as described above.

The resulting PstI-digested pEP 3.7 and PstI-digested pIBI30 were dissolved in 50 µl of ligation buffer containing 400 units of phage T4 ligase, and incubated at 4° C. for 16 hours. Then, the reaction was terminated by adding EDTA to 20 mM and heating at 65° C. for 10 minutes. Competent *E. coli* K12 XL-1 Blue (Stratagene, Inc.) were transformed with the resulting plasmids, and colonies screened as described above.

In this manner, a recombinant plasmid was derived and designated pEP 3.7/IBI30. This plasmid has the 3.7 kb PstI fragment from pEP 3.7 inserted into the PstI site of pIBI30 (see FIG. 7).

Next, single stranded DNA of pEP 3.7/IBI30 was prepared as follows.

A culture of *E. coli* K12 XL-1 Blue containing the plasmid pEP 3.7/IBI30 was used to inoculate 5.0 ml of ML media supplemented with 50 µg/ml of ampicillin and 10 µg/ml of tetracycline. The next day, 50 ml of ML media supplemented with 50 µg/ml of ampicillin and 0.001% (w/w) of thiamine was inoculated with 1.0 O.D.$_{600}$ of the overnight culture. The fresh culture was then incubated at 37° C. with shaking until the O.D.$_{600}$ was about 0.2 O.D.$_{600}$, or to $5 \times 10^7$ bacteria/ml. Next, into a fresh tube were added 0.5 ml of the above culture and M13KOS helper phage (International Biotechnologies, Inc.) at a multiplicity of infection of greater than 20. The phage was allowed to absorb to the bacteria at 37° C. for 30 minutes with gentle mixing.

The resulting infected culture was used to inoculate 50 ml of Circle Grow ™ media (Bio IOI, Inc.). supplemented with 70 µg/ml of kanamycin, 50 µg/ml of ampicillin, and 0.001% (w/v) thiamine. The culture was then incubated at 37° C. with shaking for 24 to 48 hours until a dense culture was present.

The resulting bacterial cells were pelleted in a Sorvall GSA rotor at 8,000 rpm for 30 minutes at 4° C. The supernatant containing the phage was precipitated by adding a ⅓th volume of 20% (w/v) polyethylene glycol-6000 (Sigma), 3.5M ammonium acetate solution, and incubating on ice for 30 minutes. The precipitated phage were pelleted in a GSA rotor at 9,000 rpm for 15 minutes at 4° C. Then, the pellet was thoroughly drained, and resuspended in 5.0 ml of 1×TE buffer. The resulting sample was vortexed for minutes with a ½ volume of 90% (v/v) phenol, then vortexed a further 2 minutes after adding 2.5 ml of chloroform. The phases were separated by centrifugation in a Sorvall SS-34 rotor at 15,000 rpm for 15 minutes at room temperature. The aqueous phase was removed, and the extraction repeated as above. The resulting DNA was precipitated by adding a ½ volume of 7.5M ammonium acetate and 2 volumes of ethanol. After 1 hour at −20° C. the DNA precipitate was collected by centrifugation in a Sorval SS-34 rotor at 16,000 rpm for 20 minutes at 4° C. The resulting DNA was resuspended in distilled water, then again ethanol precipitated and collected as described above. The single stranded DNA pellet was rinsed twice with ice cold 85% (v/v) ethanol, air dried, and then redissolved in 0.3 ml of distilled water.

B. Construction of pEP 3.7/IBI30 dl TK

Oligonucleotide mutagenisis was utilized to introduce a 387 bp deletion, from nucleotide position 744 to 1131 of FIG. 3, into the EHV-1 tk gene of plasmid pEP 3.7/IBI30 by a modification of the procedure of Su, T.-Z. et al. *Gene*, 69:81-89 (1988). This deletion eliminates the middle third of the EHV-1 tk gene, which includes major elements of the catalytic site of the EHV-1 tk gene. Note, this deletion avoids regions closer to adjacent gene which might adversely effect function of flanking genes.

More specifically, a 32-mer oligonucleotide having the following sequence, was synthesized and purified as described above:

5'-ACGAAAGGGGCAACTC—GTGGTAAAGCGGCTCT-3'

The first 16 nucleotides correspond to the sequence of bases 728 to 743 of the EHV-1 tk gene; whereas, the latter 16 nucleotides correspond to a sequence 387 bp downstream (see FIG. 3). The length of the "arms" of the oligonucleotide were chosen to have a hybridization temperature of 47° C. according to the formula:

$$T_H = 2° C. (A+T) + 4° C. (G+C) - 3° C.$$

The hybridization temperature was selected above the polymerization temperature so as to prevent disassociation of the primer during subsequent steps.

50 pmoles of the above 32-mer oligonucleotide were phosphorylated in 25 µl of a buffer comprising 70 mM Tris-HCl (pH 7.6), 10 mM MgCl$_2$, 5.0 mM dithiothreitol, 1.0 mM ATP, and 10 units of polynucleotide kinase at 37° C. for 30 minutes, then heat inactivated at 70° C. for 10 minutes.

Next, 0.66 pmole of the resulting phosphorylated 32-mer oligonucleotide was added to 0.2 pmole (0.9 µg)

of pEP 3.7/IBI30 single stranded DNA dissolved in 10 μl of a buffer comprising 40 mM Tris-HCl (pH 7.5), 20 mM MgCl$_2$, and 50 mM NaCl (hereinafter "T7 DNA polymerase buffer") and annealed at 65° C. for 5 minutes followed by slow cooling to 4° C. Then, the oligonucleotide was extended and the new strand sealed by adding 1.0 μl of T7 DNA polymerase (14 units of SEquence TM; U.S. BioChemical), 1.0 μl of phage T4 ligase (400 units). 1.5 μl of 10 mM ATP, 2.0 μl of a mixture of 0.5 mM dATP, 0.5 mM dGTP, 0.5 mM dCTP, 0.5 mM dTTP, and 50 μM dithiothreitol in T7 DNA polymerase buffer, and incubating at 37° C. for 15 minutes, followed by heat inactivation at 65° C. for 5 minutes.

The resulting heteroduplex DNA was separated from the parental single stranded pEP 3.7/IBI30 DNA by absorption of the latter onto nitrocellulose filter as follows.

To the above reaction mixture were added 205 μl of water and 30 μl of 0.5M NaCl. The sample was applied to a Centrex TM spin filter (Shleicher Schuell), which was centrifuged at 500×g for 10 minutes at room temperature. The nitrocellulose filter was rinsed with 100 μl of 0.5M NaCl and the above step repeated. The centrifugal eluent was dialyzed against 0.1×TE buffer, and ethanol precipitated as described above.

The resulting DNA was dissolved in 50 μl of BstEII cutting buffer and digested with 10 units of BstEII at 60° C. for 1 hour to linearize any parental plasmid pEP 3.7/IBI30, and reduce its transforming frequency. Then, the reaction was terminated by adding EDTA to 20 mM and aliquots were employed to transform competent *E. coli* K12 XL-1 Blue, and colonies were screened as described above.

In this manner, a recombinant plasmid was derived and designated pEP 3.7/IBI30 dl TK. This plasmid has a 387 bp deletion from position 744 to 1131, in the EHV-1 tk gene as expected. The deletion was verified by producing single stranded DNA and sequencing with a synthetic oligonucleotide adjacent to the deletion (see FIG. 7).

C. Construction of A Recombinant tk⁻

The particular strain chosen for the recombination was EHV-1 (β-Gal). However, as discussed above, other tk⁻EHV-1 strains or tk⁺strains could equally be employed without departing from the spirit and scope of the present invention.

In order to obtain, an EHV-1 deletion mutant in the tk gene, by homologous recombination between EHV-1 (β-Gal) and a hybrid plasmid containing a deletion in the coding region of the EHV-1 tk gene it was necessary to start with the intact. DNA of EHV-1 (β-Gal) and a hybrid plasmid containing a deletion in the coding region of the EHV-1 tk gene. The progeny virus obtained following this type of cross mainly comprise parental tk⁻EHV-1 (β-Gal). However, the tk⁻deletion recombinant virus could be identified by the loss of the β-Gal gene, which produced clear virus plaques distinct from the blue plaques of the parental tk⁻EHV-1 (β-Gal).

The hybrid plasmid chosen for the construction of the tk⁻EHV-1 deletion mutant was pEP 3.7/IBI30 dl TK. However, other hybrid plasmids containing larger or smaller deletions in other portions of the EHV-1 tk gene, could equally be employed to obtain other tk⁻EHV-1 deletion mutants without departing from the scope and spirit of this invention.

More specifically, the 3.3 kb PstI to PstI fragment from pEP 3.7/IBI30 dl TK was excised from the hybrid plasmid by adding 10 μg of pEP 3.7/IBI30 dl TK to 500 μl of PstI cutting buffer containing 100 units of PstI and digesting at 37° C. for 1 hour. Then, the reaction was terminated by digestion with Proteinase K and extracted with phenol as described above. After dialysis of the aqueous phase against 0.1×TE buffer, the resulting DNA was adjusted to 10 μg/ml and filter sterilized.

The construction of the recombinant tk⁻deletion mutant of EHV-1 was carried out as follows:

RAB-9 cells were seeded in 60 mm Petri dishes (0.2×10$^6$ cells per dish) and incubated at 37° C. for 48 hours. Then, the following sterile solutions were added to a test tube in sequential order:

(1) 0.02 ml of a 50 μg/ml solution of tk⁻EHV-1 (β-Gal) DNA in TE buffer;

(2) 0.2 ml of a 10 μg/ml solution of hybrid plasmid pEP 3.7/IBI30 dl TK digested with PstI;

(3) 0.65 ml of water;

(4) 1.0 ml of a 20 μg/ml solution of salmon sperm DNA in 2×Herpes buffer solution: and (5) 0.13 ml of 2.0M CaCl$_2$.

The resulting solution was mixed by inversion and kept at room temperature for 30 minutes while a DNA-calcium phosphate precipitate formed. Then, 0.5 ml of the suspension containing the DNA-calcium phosphate precipitate was added directly to 5.0 ml of growth medium and plated on RAB-9 cells which had been seeded in 60 mm Petri dishes 48 hours earlier. The cells were incubated at 37° C. for 4 hours. Then, the media was aspirated, and the monolayer rinsed with 5.0 ml of fresh growth media, followed by the addition of 1.0 ml of a solution comprising 1×Herpes buffer solution plus 20% (w/v) glucose plus 10% (v/v) DMSO. After a 5 minute incubation at room temperature, the solution was aspirated, and the monolayer rinsed with media again. Then, 5.0 ml of fresh growth media with 0.5×10$^6$ Vero cells, which had been prepared as a cell suspension immediately prior, was added to the transfected RAB-9 cells. The culture was incubated at 37° C. for 4 days until extensive cytopathic effects occurred. Virus harvests were made as described and stored at −80° C.

The virus harvests were then titrated in Cos-1 cells under an agar overlay as described in U.S. Pat. No. 4,514,497, with the modification that the second agar overlay had the neutral red indicator dye replaced with 0.1 mg/ml of MTT and 330 μg/ml X-Gal. Cos-1 cells (ATCC No. CRL-1650) are derived from Vero cells, and express the SV40 T antigen which increases expression of the β-Galactosidase gene under the control of SV40 early promoter. Virus plaques of the parental tk⁻virus, i.e., EHV-1 (β-Gal). were blue against a pale purple background, whereas several clear plaques were present at lower dilutions. The clear plaques were "picked" by inserting a capillary pipette into the agar over the plaque and aspirating and dispensing the material into 1.0 ml of growth medium. The "picked" plaques contained virus in an amount of from about 104 to 105 p.f.u./ml and were stored at −80° C.

Working stocks of virus from several of the "picked" clear plaques were prepared by infecting monolayer cultures of about 10$^7$ Vero cells with 1.0 ml of virus from each plaque picked and incubating at 37° C. for 2-3 days until extensive cytopathic effects were observed. A clear plaque was subjected to several cycles of plaque purification and then analyzed further.

In this manner virus clone EHV-1 (dl TK) was obtained. EHV-1 (dl TK) was been deposited with the American Type Culture Collection under ATCC No. VR-2248.

EXAMPLE 3

Analysis of EHV-1 Recombinants

A. Nucleic Acid Hybridization

Viral DNA was prepared for EHV-1 (β-Gal) and EHV-1 (dl TK) as described above. Then, 1.0 μg of viral DNA from each of the recombinant viruses was cleaved with PstI as described above, and the fragments were separated by electrophoresis on 0.6% (w/v) agarose at 35 volts (constant voltage) for 16 hours at 4° C. The electrophoresis buffer was 0.04M Trizma base (pH 8.1), 0.03M NaH and 0.001M EDTA. Restriction nuclease fragments of the parental tk+EHV-1 strain, i.e. Rhinoquin TM, and marker fragments obtained by HindIII digestion of phage φX174 RF DNA were also electrophoresed. The gels were stained with ethidium bromide and photographed as described above to reveal the DNA fragments.

A nick-translated radioactive probe to pEP 3.7 was prepared as described in U.S. Pat. No. 4,514,497 except that the plasmid in this instance contained the EHV-1 tk gene.

The gels were blotted to nitrocellulose filters and processed, and the DNA on the filters hybridized with the radioactively labeled pEP 3.7 probe as described in U.S. Pat. 4,514,497. The results demonstrated that the probe hybridized to a 3.7 kb PstI fragment from the parental tk EHV-1 strain, i.e., Rhinoquin TM, and hybridized to a 3.3 kb PstI fragment from the candidate tk−deletion mutants of EHV-1. This demonstrated that the 387 bp deletion present in pEP 3.7/IBI30 had been transferred to the viral genome, thereby generating a tk−deletion mutant of EHV-1 with a PstI fragment whose mobility was increased due to the deletion.

B. TK Activity of EHV-1 Recombinants

To verify that the insertion mutant EHV-1 (β-Gal) and the deletion mutant EHV-1 (dl TK) lacked the ability to induce functional TK activity TK induction experiments were carried out by a sensitive method which detects radioactive incorporation of $^3$H-deoxythymidine into cells.

More specifically, about 40,000 RAB(BU) cells were seeded into 8 well Lab-Tek TM slides containing 0.35 ml of growth media and incubated at 37° C. for 2 days until confluency. Then, the media was aspirated and 0.1 ml of virus inoculums at serial dilutions was added to each well. The tk+parental virus EHV-1 strain, i.e., Rhinoquin TM was used as a positive control. After a 1 hour absorption at 37° C. the inoculum was aspirated and 0.35 ml of growth media with 0.1 μg/ml of cold deoxythymidine and 5.0 μCi/ml of $^3$H-deoxythymidine was added. After a further 16 hour incubation at 37° C. the infected monolayers were rinsed with 1×GKN and fixed with methanol at room temperature. Microscopic autoradiography was performed as described above in the transient TK assay. The results demonstrated heavy deposition of silver grains over the nuclei of cells infected with the tk+Rhinoquin TM strain whereas, there were no significant number of grains deposited over mock-infected or EHV-1 (β-Gal)-infected or EHV-1 (dl TK)-infected cells. These results demonstrate that strains EHV-1 (β-Gal) and EHV-1 (dl TK) do not induce detectable TK activity, i.e., fail to produce any functional TK.

While the invention has been described in detail and with reference to specific embodiments thereof, it will be apparent to one skilled in the art that various changes and modifications can be made therein without departing from the spirit and scope thereof.

We claim:

1. The equine herpesvirus type 1 (EVH-1) which fails to produce any functional thymidine kinase as a result of a deletion, an insertion or both a deletion and an insertion in the EHV-1 thymidine kinase gene.

2. The equine herpesvirus type 1 as claimed in claim 1, wherein said insertion is about 8 to 5000 bp in size.

3. The equine herpesvirus type 1 as claimed in claim 1, wherein said deletion is about 10 to 1500 bp in size.

4. The equine herpesvirus type 1 as claimed in claim 3, wherein said deletion is about 75 to 750 bp in size.

5. The equine herpesvirus type 1 as claimed in claim 1, wherein said equine herpesvirus type 1 is temperature-resistant.

6. The equine herpesvirus type 1 as claimed in claim 1, wherein said virus has the identifying characteristics of EHV-1 (dl TK) (ATCC No. VR-2248).

7. The equine herpesvirus type 1 as claimed in claim 1, wherein said equine herpesvirus type is lyophilized.

8. The equine herpesvirus type 1 (EHV-1) which fails to produce any functional thymidine kinase as a result of an insertion in the EHV-1 thymidine kinase gene produced by the process comprising:

(1) constructing a hybrid plasmid comprising a cloning vector and a DNA fragment of EHV-1 containing substantially all of the EHV-1 thymidine kinase gene and flanking sequences thereof;

(2) inserting a detectable foreign DNA sequence within the coding region of the EHV-1 thymidine kinase gene of the hybrid plasmid of step (1);

(3) co-transfecting semi-permissive, immortalized EHV-1 host cells with the hybrid plasmid of step (2) and genomic DNA isolated from an EHV-1, wherein said genomic DNA comprises the EHV-1 thymidine kinase gene and expresses the EHV-1 thymidine kinase gene upon infection of EHV-1 host cells, wherein said semi-permissive, immortalized EHV-1 host cells are RAB-9 or RAB(BU) cells, and harvesting recombinant EHV-1;

(4) culturing the resulting recombinant EHV-1 of step (3) in permissive EHV-1 host cells;

(5) selecting or screening the cells resulting from step (4) or EHV-1 harvested therefrom, for EHV-1 containing the detectable foreign DNA sequence; and (6) screening the cells or virus from step (5) for EHV-1 which fails to produce any functional thymidine kinase as a result of an insertion in the EHV-1 thymidine kinase gene, and wherein the virus in which the insertion is demonstrated is harvested.

9. The equine herpesvirus type 1 as claimed in claim 8, wherein said insertion is about 8 to 5000 bp in size.

10. The equine herpesvirus type 1 as claimed in claim 8, wherein the genomic DNA of step (3) is isolated from a temperature-resistant equine herpesvirus type 1.

11. The equine herpesvirus type 1 as claimed in claim 8, wherein the process additionally comprises step (7):

(7) culturing the resulting equine herpesvirus type of step (6) in permissive EHV-1 host cells at a non-permissive temperature so as to select for and produce temperature-resistant equine herpesvirus type 1 mutants which fail to produce any functional thymidine kinase as a result of an insertion in the EHV-1 thymidine kinase gene.

12. The equine herpesvirus type 1 as claimed in claim 8, wherein said cloning vector is selected from the group consisting of pBR322, pBR325, pKH47, pBR328, pHC79, phage Charon 28, pKB11, pKSV-10 and pMAR420.

13. The equine herpesvirus type 1 as claimed in claim 12, wherein said cloning vector is pBR322.

14. The equine herpesvirus type 1 as claimed in claim 8, wherein said permissive equine herpesvirus type 1 host cells are selected from the group consisting of Vero cells, BHK-21 cells, equine dermal cells, equine dermis (NBL-6) cells and equine kidney cells.

15. The equine herpesvirus type 1 as claimed in claim 8, wherein the genomic DNA is isolated from an EHV-1 strain selected from the group consisting of the L-M cell adapted Kentucky A strain, the hamster adapted Kentucky A strain, the Rhinoquin ® strain, the Rhinoimmune ® strain, the Army 183 strain, the Q strain, the MS strain, the Kentucky B strain and the Kentucky D strain.

16. The equine herpesvirus type 1 as claimed in claim 8, wherein said equine herpesvirus type 1 lyophilized.

17. An equine herpesvirus type 1 (EHV-1) which fails to produce any functional thymidine kinase as a result of a deletion in the EHV-1 thymidine kinase gene produced by the process comprising:
   (1) constructing a hybrid plasmid comprising a cloning vector and a DNA fragment of EHV-1 containing substantially all of the EHV-1 thymidine kinase gene and flanking sequences thereof;
   (2) deleting sequences within the coding region of the EHV-1 thymidine kinase gene of the hybrid plasmid of step (1);
   (3) co-transfecting semi-permissive, immortalized EHV-1 host cells with the hybrid plasmid of step (2) and genomic DNA isolated from an EHV-1 which fails to produce any functional thymidine kinase as a result of an insertion of a detectable foreign DNA sequence in the EHV-1 thymidine kinase gene, wherein said semi-permissive, immortalized EHV-1 host cells are RAB-9 or RAB(BU) cells, and harvesting recombinant EHV-1;
   (4) culturing the resulting recombinant EHV-1 of step (3) in permissive EHV-1 host cells;
   (5) selecting or screening the cells resulting from step (4) or EHV-1 harvested therefrom, for EHV-1 which do not contain the detectable foreign DNA sequence insertion; and
   (6) screening the cells or virus from step (5) for EHV-1 which fails to produce any functional EHV-1 gene thymidine kinase as a result of a deletion in the EHV-1 thymidine kinase gene, and wherein virus in which the deletion is demonstrated is harvested.

18. The equine herpesvirus type 1 as claimed in claim 17, wherein said deletion is about 10 to 1500 bp in size.

19. The equine herpesvirus type 1 as claimed in claim 18, wherein said deletion is about 75 to 750 bp in size.

20. The equine herpesvirus type 1 as claimed in claim 17, wherein the genomic DNA of step (3) is isolated from a temperature-resistant equine herpesvirus type 1.

21. The equine herpesvirus virus type 1 as claimed in claim 17, wherein the process additionally comprises step (7):
   (7) culturing the resulting equine herpesvirus type 1 of step (6) in permissive EHV-1 host cells at a non-permissive temperature so as to select for and produce temperature-resistant equine herpesvirus type 1 mutants which fail to produce any functional thymidine kinase as a result of a deletion in the EHV-1 thymidine kinase gene.

22. The equine herpesvirus type 1 as claimed in claim 17, wherein said cloning vector is selected from the group consisting of pBR322, pBR325, pKH47, pBR328, pHC79, phage Charon 28, pKB11, pKSV-10 and pMAR420.

23. The equine herpesvirus type 1 as claimed in claim 22, wherein said cloning vector is pBR322.

24. The equine herpesvirus type 1 as claimed in claim 17, wherein the resulting hybrid plasmid of step (2) is pEP 3.7/IBI30 dl TK.

25. The equine herpesvirus type 1 as claimed in claim 17, wherein said permissive equine herpesvirus type 1 host cells are selected from the group consisting of Vero cells, BHK-21 cells, equine dermal cells, equine dermis (NBL-6) cells and equine kidney cells.

26. The equine herpesvirus type 1 as claimed in claim 17, wherein the genomic DNA is isolated from an EHV-1 strain selected from the group consisting of the L-M cell adapted Kentucky A strain, the hamster adapted Kentucky A strain, the Rhinoquin ® strain, the Rhinoimmun ® strain, the Army 183 strain, the Q strain, the MS strain, the Kentucky B strain and the Kentucky D strain.

27. The equine herpesvirus type 1 as claimed in claim 17, wherein said equine herpesvirus type 1 is lyophilized.

* * * * *

UNITED STATES PATENT AND TRADEMARK OFFICE
CERTIFICATE OF CORRECTION

PATENT NO. : 5,292,653

DATED : March 8, 1994

INVENTOR(S) : MALON KIT, SAUL KIT

It is certified that error appears in the above-indentified patent and that said Letters Patent is hereby corrected as shown below:

Between the Title and Field of the Invention, insert -- The invention described herein was developed during the tenure of a Research Career Award to Saul Kit from the United States Public Health Service of Department of Health and Human Services. The Government has certain rights. --

Signed and Sealed this

Eleventh Day of April, 1995

Attest:

BRUCE LEHMAN

Attesting Officer

Commissioner of Patents and Trademarks